US012128260B2

(12) United States Patent
Hatami

(10) Patent No.: US 12,128,260 B2
(45) Date of Patent: Oct. 29, 2024

(54) PATHOGEN CAPTURE USING ACTIVE SURFACE MODIFICATION

(71) Applicant: Farzin Hatami, Redwood City, CA (US)

(72) Inventor: Farzin Hatami, Redwood City, CA (US)

( * ) Notice: Subject to any disclaimer, the term of this patent is extended or adjusted under 35 U.S.C. 154(b) by 429 days.

(21) Appl. No.: 17/727,795

(22) Filed: Apr. 24, 2022

(65) Prior Publication Data

US 2022/0249885 A1 Aug. 11, 2022

Related U.S. Application Data

(63) Continuation-in-part of application No. PCT/US2021/029220, filed on Apr. 26, 2021.
(Continued)

(51) Int. Cl.
*B01D 39/14* (2006.01)
*A01N 43/38* (2006.01)
(Continued)

(52) U.S. Cl.
CPC ............ *A62B 23/025* (2013.01); *A01N 43/38* (2013.01); *A61L 9/00* (2013.01); *B01D 39/16* (2013.01);
(Continued)

(58) Field of Classification Search
CPC ...... A62B 23/025; A01N 43/38; A01N 25/34; A61L 9/00; A61L 2101/46; B01D 39/16; B01D 46/0028; B01D 2239/0442; B01D 2239/0478; B01D 2279/65; B01D 39/2017; B01D 2239/0428; B01D 2239/0464; B01D 2239/0492; A01P 1/00
(Continued)

(56) References Cited

U.S. PATENT DOCUMENTS 5,851,395 A 12/1998 Kawase et al.
6,182,659 B1 2/2001 Kawase et al.
(Continued)

FOREIGN PATENT DOCUMENTS

WO WO-03039713 A1 * 5/2003 ......... B01D 46/0001
WO 2012/094459 A1 7/2012
(Continued)

OTHER PUBLICATIONS

Casanaova et al., "Virus Transfer from Personal Protective Equipment to Healthcare Employees' Skin and Clothing," Emerging Infectious Diseases • www.cdc.gov/eid • vol. 14, No. 8 (pp. 1291-1293) Aug. 2008.
(Continued)

*Primary Examiner* — Frank M Lawrence, Jr.
(74) *Attorney, Agent, or Firm* — Enterprise Patent LLC

(57) ABSTRACT

Fabrics, such as employed in air filters, facemasks, garments, or PPE, are coated with pathogen-binding agents, such as chemicals that bind to protein-encapsulated airborne pathogens. Some of these pathogen-binding agents include multifunctional chemicals that bind to the fabrics and to exposed proteins and/or glycans on the pathogens. Some of these pathogen-binding agents include multifunctional silanes. Some of these pathogen-binding agents include multifunctional phosphanes or phosphonates.

20 Claims, 12 Drawing Sheets

Related U.S. Application Data

(60) Provisional application No. 63/254,273, filed on Oct. 11, 2021, provisional application No. 63/017,460, filed on Apr. 29, 2020.

(51) Int. Cl.

| | | |
|---|---|---|
| *A61L 9/00* | (2006.01) | |
| *A62B 23/02* | (2006.01) | |
| *B01D 39/16* | (2006.01) | |
| *B01D 46/00* | (2022.01) | |
| *A01P 1/00* | (2006.01) | |
| *A61L 101/46* | (2006.01) | |

(52) U.S. Cl.
CPC ............ B01D 46/0028 (2013.01); *A01P 1/00* (2021.08); *A61L 2101/46* (2020.08); *B01D 2239/0442* (2013.01); *B01D 2239/0478* (2013.01); *B01D 2279/65* (2013.01)

(58) Field of Classification Search
USPC ........................ 128/863; 95/285; 96/223, 226
See application file for complete search history.

(56) References Cited

U.S. PATENT DOCUMENTS

| | | |
|---|---|---|
| 6,802,891 B2 | 10/2004 | Kritzler |
| 7,044,993 B1 | 5/2006 | Bolduc |
| 7,067,194 B2 | 6/2006 | Moa et al. |
| 7,470,548 B2 | 12/2008 | Ozawa et al. |
| 8,124,169 B2 | 2/2012 | Ylitalo et al. |
| 8,678,002 B2 | 3/2014 | Stewart et al. |
| 9,539,532 B2 | 1/2017 | Fox et al. |
| 2004/0050254 A1 | 3/2004 | Tanaka et al. |
| 2006/0021302 A1 | 2/2006 | Bernard |
| 2012/0241319 A1 | 9/2012 | Carlson et al. |
| 2021/0337800 A1* | 11/2021 | Shaffer .............. A41D 13/1192 |
| 2023/0097006 A1* | 3/2023 | Gong .................... A01N 33/12 |
| | | 424/404 |

FOREIGN PATENT DOCUMENTS

| | | |
|---|---|---|
| WO | 2012/123446 A1 | 9/2012 |
| WO | 2020/123446 A1 | 4/2020 |

OTHER PUBLICATIONS

Yuan Liu et al., "Aerodynamic analysis of SARS-CoV-2 in two Wuhan hospitals," Nature , vol. 582, (pp. 557-582) Jun. 25, 2020 (Apr. 27, 2020).

Lustig et al., "E ectiveness of Common Fabrics to Block Aqueous Aerosols of Virus-like Nanoparticles," ACS Nano 2020, 14, 7651-7658 (May 21, 2020).

Van Doremalen et al., "Aerosol and Surface Stability of SARS-CoV-2 as Compared with SARS-CoV-1," n engl j med 382;16 nejm.org (Apr. 16, 2020).

Xue et al., "All Surfaces Are Not Equal in Contact Transmission of SARS-CoV-2," Matter 3, 1433-1441, (Nov. 4, 2020).

Zangmeister et al., "Filtration E ciencies of Nanoscale Aerosol by Cloth Mask Materials Used to Slow the Spread of SARS-CoV ," ACS Nano 2020, 14, 9188-9200 (Jun. 25, 2020).

International Search Report for PCT/US2021/029220 (Sep. 1, 2021).
Results of Search of US Patent Collection, Mar. 15, 2021.

* cited by examiner

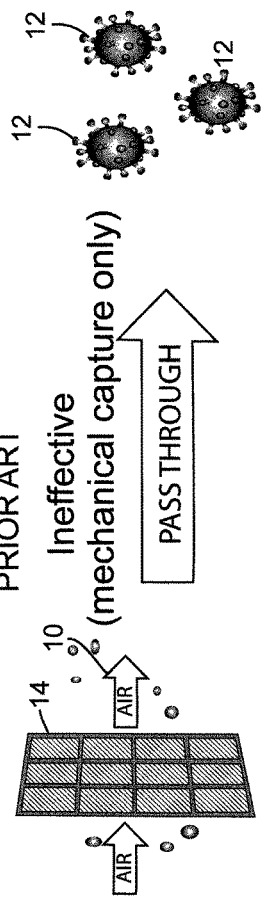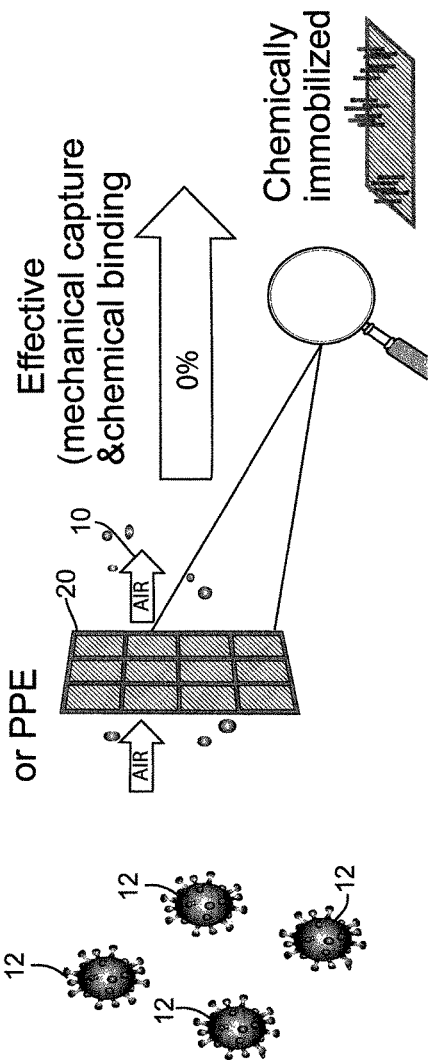

FIG. 2A

TABLE 1A

| Reference Code | Internal Code | Formula | Common Name | Other Name(s) | Structure | Comments |
|---|---|---|---|---|---|---|
| SIG5840.0 | CCH4502 | $C_9H_{20}O_5Si$ | (3-glycidoxypropyl)trimethoxysilane | 3-(2,3-epoxypropoxy)propyltrimethoxysilane; trimethoxy-[3-(oxiran-2-yl)methoxy)propyl]silane; 3-(trimethoxysilyl)propyl glycidyl ether; GLYMO | 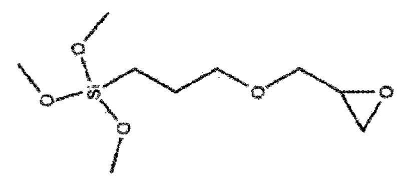 | Epoxy functional trialkoxy silane |
| SIA0590.5 | CCH9021 | $C_{11}H_{28}N_2O_3Si$ | N-(2-aminoethyl)-3-aminopropyltriethoxysilane | N-(2-aminoethyl)-3-aminopropyltriethoxysilane; N-[3-(triethoxysilyl)propyl]-1,2-ethanediamine; N-[3-(triethoxysilyl)propyl]ethylenediamine | 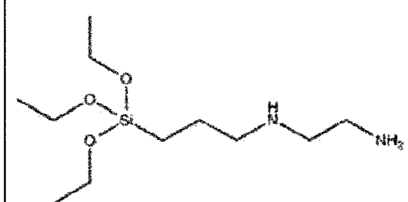 | Diamino functional trialkoxy silane |
| SIA0611.0 | CCH1053 | $C_6H_{17}NO_3Si$ | 3-aminopropyltrimethoxysilane | 3-aminopropyltrimethoxysilane, trimethoxysilylpropylamine, ?-aminopropyltrimethoxysilane, APTES, AMEO, GAPS, A-1100 | 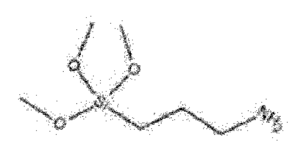 | Monoamine functional trialkoxy silane |

FIG. 2B

TABLE 1B

| Reference Code | Short Hand | Formula | Common Name | Other Name(s) | Structure | Comments |
|---|---|---|---|---|---|---|
| SIT8189.8 | CCH8845 | $C_{13}H_{25}NO_6Si$ | triethoxysilylpropylmaleamic acid | | 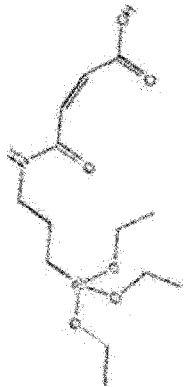 | Carboxylate functional trialkoxyl silane |
| SIA0588.0 | CCH17654 | $C_{14}H_{26}N_2O_3Si$ | (aminoethylamino methyl)phenethyltrimethoxysilane | (aminoethylaminomethyl)phenethyltrimethoxysilane, [N-(2-aminoethyl) aminomethylphenyl] ethyltrimethoxysilane, N-1-[[[2-(trimethoxysilyl)ethyl]phenyl]methyl-1-2-ethanediamine | 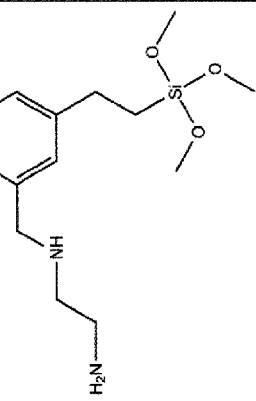 | Diamino functional trialkoxy silane |
| SID3546.92 | CCH699020 | $C_{11}H_{28}N_2O_2Si$ | 3-(N,N-dimethyl aminopropyl) aminopropylmethyldimethoxysilane | 3-(N,N-dimethylaminopropyl) aminopropylmethyldimethoxysilane; N3-[3-(dimethoxymethylsilyl)propyl]-N1,N1-dimethyl-1,3-propanediamine | 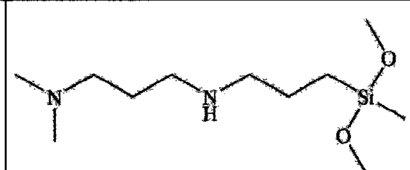 | Tertiary amino functional trialkoxy silane |

FIG. 2C

TABLE 1C

| Reference Code | Short Hand | Formula | Common Name | Other Name(s) | Structure | Comments |
|---|---|---|---|---|---|---|
| SIA0777.0 | CCH51082 | $C_9H_{21}N_3O_3Si$ | 3-azidopropyltriethoxysilane | 3-azidopropyltriethoxysilane; trimethoxysilylpropylazide | 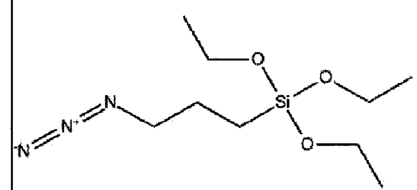 | Azide functional trialkoxy silane |
| SIT8174.0 | CCH0120 | $C_8H_4Cl_3F_{13}Si$ | (Tridecafluoro-1,1,2,2-tetrahydrooctyl)tri chlorosilane | FOTS | 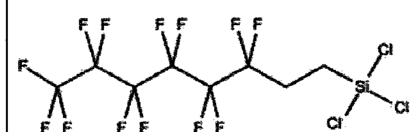 | Hydrophobic |

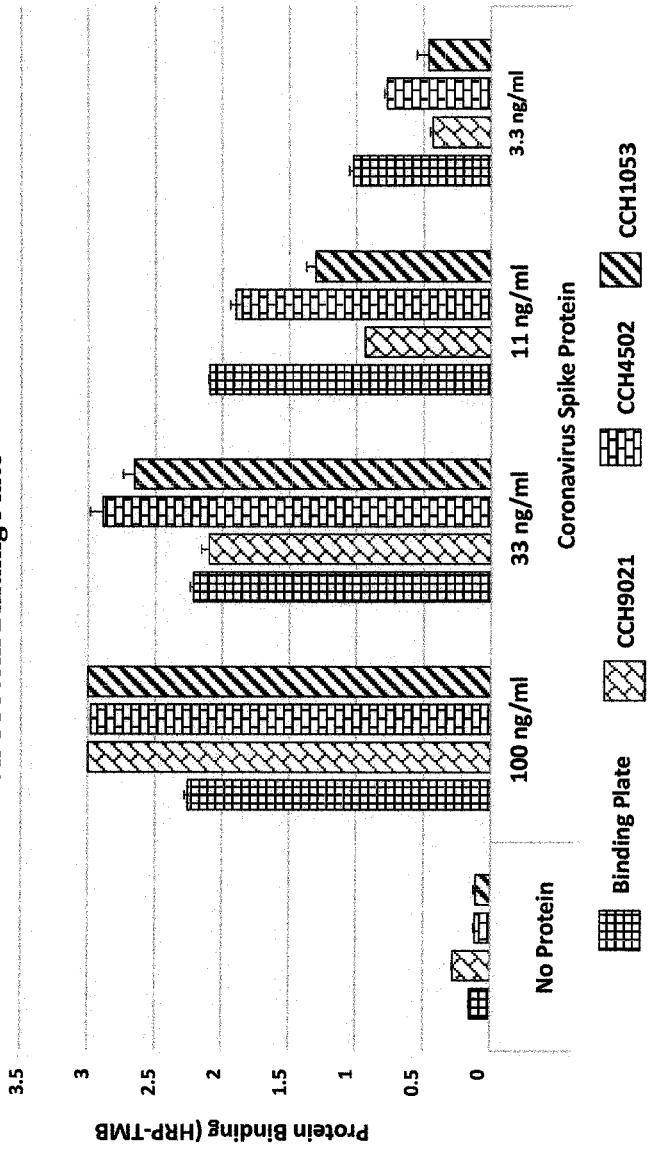

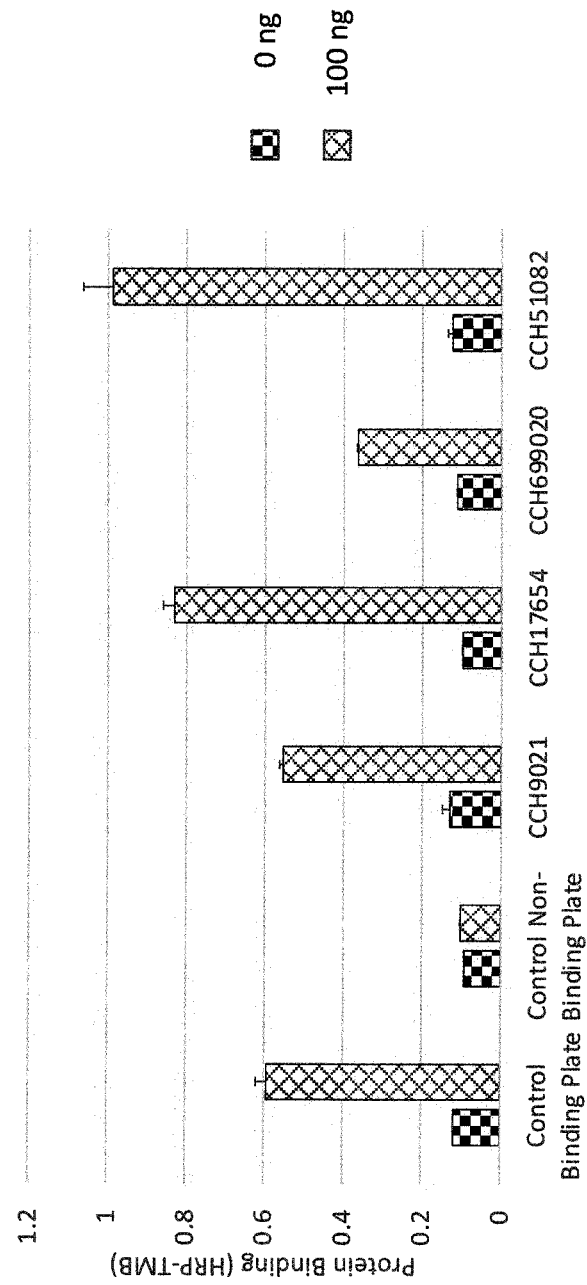

Efficient Capture of Model Protein with Nano Coated Face Masks

FIG. 8A
TABLE 2A

| Formula | Common Name | Other Name(s) | Structure | Comments |
|---|---|---|---|---|
| C₉H₂₀O₅P | (3- glycidoxypropyl) trimethoxyphosphane | 3-(2,3-epoxypropoxy)propyltrimethoxyphosphane; trimethoxy-[3-(oxiran-2-ylmethoxy)propyl] phosphane ; 3-(trimethoxyphosphyl)propyl glycidyl ether; GLYMO | | Epoxy functional trialkoxy phosphane |
| C₁₁H₂₈N₂O₃P | N-(2-aminoethyl)-3-aminopropyltriethoxyphosphane | N-(2-aminoethyl)-3-aminopropyltriethoxyphosphane; N-[3-(triethoxysilyl)propyl]-1,2-ethanediamine; N-[3-(triethoxyphosphyl)propyl]-ethylenediamine | | Diamino functional trialkoxy phosphane |
| C₆H₁₇NO₃P | 3-aminopropyltrimethoxyphosphane | 3-aminopropyltrimethoxyphosphane, trimethoxyphosphylpropylamine, 2-aminopropyltrimethoxyphosphane, APTEP, AMEO, GAPP, A-1100 | | Monoamine functional trialkoxy phosphane |

FIG. 8B
TABLE 2B

| Formula | Common Name | Other Name(s) | Structure | Comments |
|---|---|---|---|---|
| $C_{13}H_{25}NO_6P$ | triethoxyphosphyl propylmaleamic acid | | 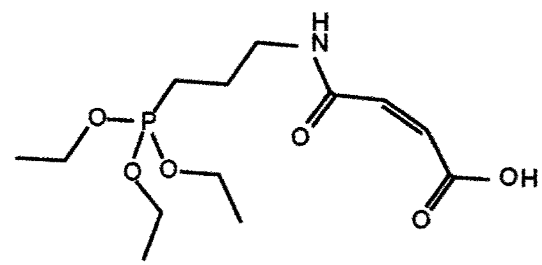 | Carboxylate functional trialkoxyl phosphane |
| $C_{14}H_{26}N_2O_3P$ | (aminoethylamino methyl)phenethylt rimethoxyphosph ane | (aminoethylaminomethyl)phe nethyltrimethoxyphosphane, [N-(2-aminoethyl)aminomethylphe nyl]ethyltrimethoxyphosphan e, N-1-[[[2-(trimethoxyphosphyl)ethyl]ph enyl]methyl-1-2-ethanediamine | 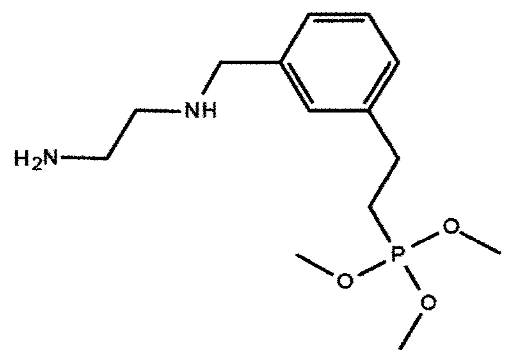 | Diamino functional trialkoxy phosphane |
| $C_{11}H_{28}N_2O_2P$ | 3-(N,N-dimethylaminopro pyl)aminopropylm ethyldimethoxyph osphane | 3-(N,N-dimethylaminopropyl)aminop ropylmethyldimethoxyphosp hane; N3-[3-(dimethoxymethylphosphyl)p ropyl]-N1,N1-dimethyl-1,3-propanediamine | 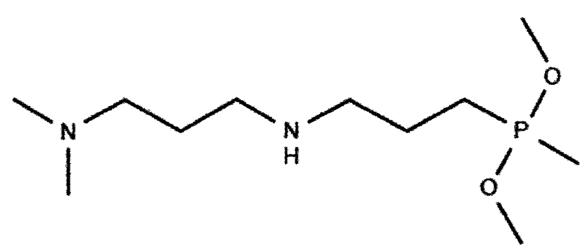 | Tertiary amino functional trialkoxy phosphane |

FIG. 8C

TABLE 2C

| Formula | Common Name | Other Name(s) | Structure | Comments |
|---|---|---|---|---|
| C₉H₂₁N₃O₃P | 3-azidopropyltriethoxyphosphane | 3-azidopropyltriethoxyphosphane; trimethoxyphosphylpropylazide | (structure shown) | Azide functional trialkoxy phosphane |
| C₈H₄Cl₃F₁₃P | (Tridecafluoro-1,1,2,2-tetrahydrooctyl)trichlorophosphane | FOTP | (structure shown) | Hydrophobic |

PATHOGEN CAPTURE USING ACTIVE SURFACE MODIFICATION

CROSS REFERENCE TO RELATED APPLICATION

This application is a continuation-in-part of International Application No. PCT/US2021/29220, which was filed on Apr. 26, 2021, which claims priority from U.S. Provisional Application No. 63/017,460, which was filed on Apr. 29, 2020; and this application claims priority from U.S. Provisional Application No. 63/254,273, which was filed on, Oct. 11, 2021; and the contents of all these applications are herein incorporated by reference in their entirety for all purposes.

TECHNICAL FIELD

The field of this disclosure relates generally to capture of airborne pathogens and, in particular, to methods, treatments, and/or materials for facilitating binding of airborne pathogens, such as viruses, bacteria, and fungi to a fabric.

BACKGROUND INFORMATION

Standard protective materials including air filters, personal protective equipment (PPE) (such as masks and medical and military grade protective apparel), and a variety of similar products employ mechanical means to block the flow of airborne particles through the materials based on the size of the particles. These protective materials reduce exposure to airborne pathogens but inadequately safeguard against harmful pathogens, including COVID-19. (See Liu, Y., et al., "Aerodynamic analysis of SARS-CoV-2 in two Wuhan hospitals" *Nature,* 2020. 582(7813): p. 557-560 and Xue, X., et al., "All Surfaces Are Not Equal in Contact Transmission of SARS-CoV-2" *Matter,* 2020. 3(5): p. 1433-1441.) Moreover, protective materials may become saturated with a range of pathogenic bacteria and viruses during typical use; and, upon doffing and disposal, these materials turn into one of the main sources of transmitting the same microorganisms in the air and infecting handling personnel. (See Casanova, L., et al., "Virus transfer from personal protective equipment to healthcare employees' skin and clothing" *Emerg Infect Dis,* 2008. 14(8): p. 1291-3.)

HEPA (High-Efficiency Particulate Air) filters are considered gold standard and are relatively effective in removing pathogens from the air. (See Malaithao, K., et al., "Evaluation of an electronic air filter for filtrating bacteria and viruses from indoor air" *Southeast Asian J Trop Med Public Health,* 2009. 40(5): p. 1113-20.) However, due to the high cost of these filters, they are typically used only in more specialized settings such as hospitals and airlines, and they are not broadly used in places of most public gatherings (schools, churches, hotel rooms, cruise line cabins, etc.) or in homes. The less expensive, non-HEPA filters which are typically found in homes and other public buildings do not effectively remove biological pathogens from the air. Given that most highly infectious viruses have a very low median infectious dose, even low levels of viral filter penetration represent a significant risk to human health. (See Brian Heimbuch; C. Y. Wu; Joseph Wander, "Viral Penetration of High Efficiency Particulate Air (HEPA) Filters" Air Force Research Laboratory, 2009(AFRL-RX-TY-TP-2009-4567).) Additionally, some viruses (including coronaviruses) remain in the air for up to 3 hours and are infectious for several days on surfaces. (See van Doremalen, N., et al., "Aerosol and surface stability of HCoV-19 (SARS-CoV-2) compared to SARS-CoV-1" *N Engl J Med,* 2020. 16: p. 1564-1567.) For this reason, handling and disposing of used filters (including HEPA filters) can also result in the redistribution of these pathogens back into the air.

OVERVIEW OF DISCLOSURE

One aspect of this disclosure relates to a method or coating for permanently bonding one or more different pathogens, including an airborne protein-encapsulated pathogen, to a medium such as a fabric.

Another aspect of this disclosure relates to a method or coating for permanently bonding one or more different pathogens, including an airborne virus, an airborne bacteria, or an airborne fungus, to a fabric such as in the form of a filter or a garment.

In some embodiments, a pathogen-capturing material for binding airborne pathogens comprises a fabric treated with a pathogen-binding chemical, wherein the pathogen-binding chemical comprises a multifunctional molecule, including at least a first functional group and a second functional group, wherein the first functional group is bonded to the fabric and the second functional group is configured to bond to a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical comprises a multifunctional silane, including at least a first functional group and a second functional group, wherein the first functional group is bonded to the fabric and the second functional group is configured to bond to a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical comprises a multifunctional molecule, including at least a first functional group and a second functional group, wherein the first functional group is bonded to the fabric and the second functional group is configured to bond to a protein-encapsulated airborne pathogen, wherein the first functional group or second functional group comprises one or more of an amino group, an epoxy group, a carboxylate group, and an azide group.

In some additional, alternative, or selectively cumulative embodiments, a pathogen-capturing material for binding airborne pathogens comprises a fabric treated with a pathogen-binding chemical, wherein the pathogen-binding chemical comprises a multifunctional silane, including at least a first functional group and a second functional group, wherein the first functional group is bonded to the fabric and the second functional group is configured to bond to a protein-encapsulated airborne pathogen, wherein the first functional group or second functional group comprises one or more of an amino group, an epoxy group, a carboxylate group, and an azide group.

In some additional, alternative, or selectively cumulative embodiments, a pathogen-capturing material for binding airborne pathogens, comprises a fabric treated with a pathogen-binding chemical, wherein the pathogen-binding chemical comprises a multifunctional silane, including at least a first functional group and a second functional group, wherein the first functional group is bonded to the fabric and the second functional group is configured to bond to a protein-encapsulated airborne pathogen, wherein the first functional group or second functional group comprises one or more of an amino group, an epoxy group, a carboxylate group, and an azide group.

In some additional, alternative, or selectively cumulative embodiments, a pathogen-capturing material for binding airborne pathogens comprises a fabric treated with a pathogen-binding chemical, wherein the pathogen-binding chemical comprises a bifunctional silane, including at least a first functional group and a second functional group, wherein the first functional group is bonded to the fabric and the second functional group is configured to bond to a protein-encapsulated airborne pathogen, wherein the first functional group or second functional group comprises one or more of an amino group, an epoxy group, a carboxylate group, and an azide group.

In some additional, alternative, or selectively cumulative embodiments, a pathogen-capturing material for binding airborne pathogens comprises a fabric treated with a pathogen-binding chemical, wherein the pathogen-binding chemical comprises a bifunctional silane having one or more of an organo-functional amino group and an epoxy group, either one of which is configured to covalently bond to a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical comprises a bifunctional silane having one or more of an organo-functional amino group and an epoxy group, either one of which is configured to covalently bond to a protein or a glycan on a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical comprises a bifunctional silane having one or more of an organo-functional amino group and an epoxy group, either one of which is configured to covalently bond to a protein or a glycan on a protein-encapsulated airborne pathogen, and where the bifunctional silane is configured to bond to oxygen on the fabric.

In some additional, alternative, or selectively cumulative embodiments, a pathogen-capturing material for binding airborne pathogens comprises a fabric treated with a virus-binding chemical, wherein the virus-binding chemical comprises a bifunctional silane having one or more of an organo-functional amino group and an epoxy group, either one of which is configured to covalently bond to a virus protein or a virus glycan.

In some additional, alternative, or selectively cumulative embodiments, a pathogen-capturing material for binding airborne pathogens comprises a fabric treated with a pathogen-binding chemical, wherein the fabric is configured in a form of a filter medium that is configured to allow air to pass therethrough, wherein the pathogen-binding chemical comprises a bifunctional silane having one or more of an organo-functional amino group and an epoxy group, either one of which is configured to covalently bond to covalently bond to a protein-encapsulated airborne pathogen.

In some additional, alternative, or selectively cumulative embodiments, a pathogen-capturing material for binding airborne pathogens comprises a fabric treated with a virus-binding chemical, wherein the fabric is configured in a form of a filter medium that is configured to allow air to pass therethrough, wherein the virus-binding chemical comprises a bifunctional silane having one or more of an organo-functional amino group and an epoxy group, either one of which is configured to covalently bond to a virus protein or a virus glycan.

In some additional, alternative, or selectively cumulative embodiments, a coating fluid for treating a fabric comprises a pathogen-binding chemical including a multifunctional or bifunctional silane having one or more of an organo-functional amino group and an epoxy group, either one of which is configured to covalently bond to a protein or a glycan on a protein-encapsulated airborne pathogen.

In some additional, alternative, or selectively cumulative embodiments, a coating fluid for treating a fabric comprises a pathogen-binding chemical including a multifunctional or bifunctional silane including at least a first functional group and a second functional group, wherein the first functional group is configured to bond to the fabric and the second functional group is configured to bond to a protein-encapsulated airborne pathogen, wherein the first functional group or the second functional group comprises an organo-functional amino group and an epoxy group.

In some additional, alternative, or selectively cumulative embodiments, a coating fluid for treating a fabric comprises a pathogen-binding chemical including a multifunctional or bifunctional silane including at least a first functional group and a second functional group, wherein the first functional group is configured to bond to the fabric and the second functional group is configured to bond to a protein-encapsulated airborne pathogen, wherein the second functional group comprises an organo-functional amino group, an epoxy group, a carboxylate group, and an azide group, any one of which is configured to bond to a protein or a glycan on a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical is configured to independently bind IgG and a protein or a glycan on a protein-encapsulated airborne pathogen.

In some additional, alternative, or selectively cumulative embodiments, a pathogen-capturing material for binding airborne pathogens comprises a fabric treated with a virus-binding chemical, wherein the virus-binding chemical is configured to independently bind IgG and an airborne pathogen.

In some additional, alternative, or selectively cumulative embodiments, a virus-removing filter comprises a virus-capturing body containing one or more pathogen-binding chemicals including at least one of 3-aminopropyltriethoxysilane ($C_9H_{23}NO_3Si$), (3-glycidoxypropyl)trimethoxysilane ($C_9H_{20}O_5Si$), N-(2-aminoethyl)-3-aminopropyltriethoxysilane ($C_{11}H_{28}N_2O_3Si$), 3-aminopropyltrimethoxysilane ($C_6H_{17}NO_3Si$), triethoxysilylpropylmaleamic acid ($C_{13}H_{25}NO_6Si$), (aminoethylaminomethyl)phenethyltrimethoxysilane ($C_{14}H_{26}N_2O_3Si$), 3-(N,N-dimethylaminopropyl)aminopropylmethyldimethoxysilane ($C_{11}H_{28}N_2O_2Si$), and 3-azidopropyltriethoxysilane ($C_9H_{21}N_3O_3Si$), maleamic acid, calixarene, and an alkylsilane.

In some additional, alternative, or selectively cumulative embodiments, a pathogen-capturing material for binding airborne pathogens comprises a fabric treated with a pathogen-binding chemical, wherein the pathogen-binding chemical comprises one or more of 3-aminopropyltriethoxysilane ($C_9H_{23}NO_3Si$), (3-glycidoxypropyl)trimethoxysilane ($C_9H_{20}O_5Si$), N-(2-aminoethyl)-3-aminopropyltriethoxysilane ($C_{11}H_{28}N_2O_3Si$), 3-aminopropyltrimethoxysilane ($C_6H_{17}NO_3Si$), triethoxysilylpropylmaleamic acid ($C_{13}H_{25}NO_6Si$), (aminoethylaminomethyl)phenethyltrimethoxysilane ($C_{14}H_{26}N_2O_3Si$), 3-(N,N-dimethylaminopropyl)aminopropylmethyldimethoxysilane ($C_{11}H_{28}N_2O_2Si$), and 3-azidopropyltriethoxysilane ($C_9H_{21}N_3O_3Si$), maleamic acid, calixarene, and an alkylsilane.

In some additional, alternative, or selectively cumulative embodiments, a pathogen-capturing material for binding airborne pathogens comprises a fabric treated with a pathogen-binding chemical, wherein the fabric is configured in a form of a filter medium that is configured to allow air to pass therethrough, wherein the pathogen-binding chemical comprises one or more of the pathogen-binding chemical comprises one or more of 3-aminopropyltriethoxysilane ($C_9H_{23}NO_3Si$), (3-glycidoxypropyl)trimethoxysilane ($C_9H_{20}O_5Si$), N-(2-aminoethyl)-3-aminopropyltriethoxysilane ($C_{11}H_{28}N_2O_3Si$), 3-aminopropyltrimethoxysilane ($C_6H_{17}NO_3Si$), triethoxysilylpropylmaleamic acid ($C_{13}H_{25}NO_6Si$), (aminoethylaminomethyl)phenethyltrimethoxysilane ($C_{14}H_{26}N_2O_3Si$), 3-(N,N-dimethylaminopropyl)aminopropylmethyldimethoxysilane ($C_{11}H_{28}N_2O_2Si$), and 3-azidopropyltriethoxysilane ($C_9H_{21}N_3O_3Si$), maleamic acid, calixarene, and an alkylsilane.

In some additional, alternative, or selectively cumulative embodiments, a method of for making the pathogen-capturing material comprises: providing a fabric; and treating the fabric with a pathogen-binding chemical, wherein the pathogen-binding chemical comprises a multifunctional silane, including at least a first functional group and a second functional group, wherein the first functional group is configured to bond to the fabric and the second functional group is configured to bond to a protein-encapsulated airborne pathogen.

In some additional, alternative, or selectively cumulative embodiments, a method of for making the pathogen-capturing material comprises: providing a fabric; and treating the fabric with a pathogen-binding chemical, wherein the pathogen-binding chemical comprises a multifunctional silane, including at least a first functional group and a second functional group, wherein the first functional group is configured to bond to the fabric and the second functional group is configured to bond to a protein-encapsulated airborne pathogen, wherein the first functional group or second functional group comprises one or more of an amino group, an epoxy group, a carboxylate group, and an azide group which is configured to bond to a protein or a glycan on a protein-encapsulated airborne pathogen.

In some additional, alternative, or selectively cumulative embodiments, a method for capturing airborne pathogens comprises: providing a fabric treated with a pathogen-binding chemical, wherein the pathogen-binding chemical comprises a multifunctional silane having one or more of amino group, an epoxy group, a carboxylate group, and an azide group, any one of which is configured to covalently bond to a protein or a glycan on a protein-encapsulated airborne pathogen, wherein the fabric has opposing first and second sides; and causing air to sequentially pass through the first and second sides of the fabric; wherein prior to entering the first side of the fabric, the air has a measurable amount of protein-encapsulated airborne pathogens that are contagious to humans; wherein the amino group, the epoxy group, the carboxylate group, or the azide group of the pathogen-binding chemical of the fabric binds protein-encapsulated airborne pathogens flowing through the fabric; and wherein the air exiting the second side of the fabric contains no measurable amount of protein-encapsulated airborne pathogens that are contagious to humans.

In some additional, alternative, or selectively cumulative embodiments, a pathogen-capturing material for binding airborne pathogens, produced by a process comprising: providing a fabric; and treating the fabric with a pathogen-binding chemical, wherein the pathogen-binding chemical comprises a multifunctional silane, including at least a first functional group and a second functional group, wherein the first functional group is configured to bond to the fabric and the second functional group is configured to bond to a protein-encapsulated airborne pathogen, wherein the first functional group or second functional group comprises one or more of an amino group, an epoxy group, a carboxylate group, and an azide group which is configured to bond to a protein or a glycan on a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical comprises a multifunctional phosphane or a multifunctional phosphonate, including at least a first functional group and a second functional group, wherein the first functional group is bonded to the fabric and the second functional group is configured to bond to a protein-encapsulated airborne pathogen, wherein the first functional group or second functional group comprises one or more of an amino group, an epoxy group, a carboxylate group, and an azide group.

In some additional, alternative, or selectively cumulative embodiments, a pathogen-capturing material for binding airborne pathogens, comprises a fabric treated with a pathogen-binding chemical, wherein the pathogen-binding chemical comprises a multifunctional phosphane or a multifunctional phosphonate, including at least a first functional group and a second functional group, wherein the first functional group is bonded to the fabric and the second functional group is configured to bond to a protein-encapsulated airborne pathogen, wherein the first functional group or second functional group comprises one or more of an amino group, an epoxy group, a carboxylate group, and an azide group.

In some additional, alternative, or selectively cumulative embodiments, a pathogen-capturing material for binding airborne pathogens comprises a fabric treated with a pathogen-binding chemical, wherein the pathogen-binding chemical comprises a bifunctional phosphane or a bifunctional phosphonate, including at least a first functional group and a second functional group, wherein the first functional group is bonded to the fabric and the second functional group is configured to bond to a protein-encapsulated airborne pathogen, wherein the first functional group or second functional group comprises one or more of an amino group, an epoxy group, a carboxylate group, and an azide group.

In some additional, alternative, or selectively cumulative embodiments, a pathogen-capturing material for binding airborne pathogens comprises a fabric treated with a pathogen-binding chemical, wherein the pathogen-binding chemical comprises a bifunctional phosphane or a bifunctional phosphonate having one or more of an organo-functional amino group and an epoxy group, either one of which is configured to covalently bond to a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical comprises a bifunctional phosphane or a bifunctional phosphonate having one or more of an organo-functional amino group and an epoxy group, either one of which is configured to covalently bond to a protein or a glycan on a protein-encapsulated airborne pathogen.

In some additional, alternative, or selectively cumulative embodiments, a pathogen-capturing material for binding airborne pathogens comprises a fabric treated with a pathogen-binding chemical, wherein the pathogen-binding chemical comprises a bifunctional phosphane or a bifunctional phosphonate having one or more of an organo-functional amino group and an epoxy group, either one of which is configured to covalently bond to a protein or a glycan on a protein-encapsulated airborne pathogen, and where the bifunctional phosphane or a bifunctional phosphonate is configured to bond to oxygen on the fabric.

In some additional, alternative, or selectively cumulative embodiments, a pathogen-capturing material for binding airborne pathogens comprises a fabric treated with a virus-binding chemical, wherein the virus-binding chemical comprises a bifunctional phosphane or a bifunctional phosphonate having one or more of an organo-functional amino group and an epoxy group, either one of which is configured to covalently bond to a virus protein or a virus glycan.

In some additional, alternative, or selectively cumulative embodiments, a pathogen-capturing material for binding airborne pathogens comprises a fabric treated with a pathogen-binding chemical, wherein the fabric is configured in a form of a filter medium that is configured to allow air to pass therethrough, wherein the pathogen-binding chemical comprises a bifunctional phosphane or a bifunctional phosphonate having one or more of an organo-functional amino group and an epoxy group, either one of which is configured to covalently bond to covalently bond to a protein-encapsulated airborne pathogen.

In some additional, alternative, or selectively cumulative embodiments, a pathogen-capturing material for binding airborne pathogens comprises a fabric treated with a virus-binding chemical, wherein the fabric is configured in a form of a filter medium that is configured to allow air to pass therethrough, wherein the virus-binding chemical comprises a bifunctional phosphane or a bifunctional phosphonate having one or more of an organo-functional amino group and an epoxy group, either one of which is configured to covalently bond to a virus protein or a virus glycan.

In some additional, alternative, or selectively cumulative embodiments, a coating fluid for treating a fabric comprises a pathogen-binding chemical including a multifunctional or bifunctional phosphane or a bifunctional phosphonate having one or more of an organo-functional amino group and an epoxy group, either one of which is configured to covalently bond to a protein or a glycan on a protein-encapsulated airborne pathogen.

In some additional, alternative, or selectively cumulative embodiments, a coating fluid for treating a fabric comprises a pathogen-binding chemical including a multifunctional or bifunctional phosphane or a multifunctional or bifunctional phosphonate including at least a first functional group and a second functional group, wherein the first functional group is configured to bond to the fabric and the second functional group is configured to bond to a protein-encapsulated airborne pathogen, wherein the first functional group or the second functional group comprises an organo-functional amino group and an epoxy group.

In some additional, alternative, or selectively cumulative embodiments, a coating fluid for treating a fabric comprises a pathogen-binding chemical including a multifunctional or bifunctional phosphane or a multifunctional or bifunctional phosphonate including at least a first functional group and a second functional group, wherein the first functional group is configured to bond to the fabric and the second functional group is configured to bond to a protein-encapsulated airborne pathogen, wherein the second functional group comprises an organo-functional amino group, an epoxy group, a carboxylate group, and an azide group, any one of which is configured to bond to a protein or a glycan on a protein-encapsulated airborne pathogen.

In some additional, alternative, or selectively cumulative embodiments, a virus-removing filter comprises a virus-capturing body containing one or more pathogen-binding chemicals including at least one of 3-aminopropyltriethoxyphosphane ($C_9H_{23}NO_3P$), (3-glycidoxypropyl)trimethoxyphosphane ($C_9H_{20}O_5P$), N-(2-aminoethyl)-3-aminopropyltriethoxyphosphane ($C_{11}H_{28}N_2O_3P$), 3-aminopropyltrimethoxyphosphane ($C_6H_{17}NO_3P$), triethoxyphosphylpropylmaleamic acid ($C_{13}H_{25}NO_6P$), (aminoethylaminomethyl)phenethyltrimethoxyphosphane ($C_{14}H_{26}N_2O_3P$), 3-(N,N-dimethylaminopropyl)aminopropylmethyldimethoxyphosphane ($C_1H_{28}N_2O_2P$), and 3-azidopropyltriethoxyphosphane ($C_9H_{21}N_3O_3P$), and an alkylphosphane or an alkylphosphonate.

In some additional, alternative, or selectively cumulative embodiments, a pathogen-capturing material for binding airborne pathogens comprises a fabric treated with a pathogen-binding chemical, wherein the pathogen-binding chemical comprises one or more of 3-aminopropyltriethoxyphosphane ($C_9H_{23}NO_3P$), (3-glycidoxypropyl)trimethoxyphosphane ($C_9H_{20}O_5P$), N-(2-aminoethyl)-3-aminopropyltriethoxyphosphane ($C_{11}H_{28}N_2O_3P$), 3-aminopropyltrimethoxyphosphane ($C_6H_{17}NO_3P$), triethoxysphosphylpropylmaleamic acid ($C_{13}H_{25}NO_6P$), (aminoethylaminomethyl)phenethyltrimethoxyphosphane ($C_{14}H_{26}N_2O_3P$), 3-(N,N-dimethylaminopropyl)aminopropylmethyldimethoxyphosphane ($C_1H_{28}N_2O_2P$), and 3-azidopropyltriethoxyphosphane ($C_9H_{21}N_3O_3P$), and an alkylphosphane or an alkylphosphonate.

In some additional, alternative, or selectively cumulative embodiments, a pathogen-capturing material for binding airborne pathogens comprises a fabric treated with a pathogen-binding chemical, wherein the fabric is configured in a form of a filter medium that is configured to allow air to pass therethrough, wherein the pathogen-binding chemical comprises one or more of the pathogen-binding chemical comprises one or more of 3-aminopropyltriethoxyphosphane ($C_9H_{23}NO_3P$), (3-glycidoxypropyl)trimethoxyphosphane ($C_9H_{20}O_5P$), N-(2-aminoethyl)-3-aminopropyltriethoxyphosphane ($C_{11}H_{28}N_2O_3P$), 3-aminopropyltrimethoxyphosphane ($C_6H_{17}NO_3P$), triethoxyphosphylpropylmaleamic acid ($C_{13}H_{25}NO_6P$), (aminoethylaminomethyl)phenethyltrimethoxyphosphane ($C_{14}H_{26}N_2O_3P$), 3-(N,N-dimethylaminopropyl)aminopropylmethyldimethoxyphosphane ($C_1H_{28}N_2O_2P$), and 3-azidopropyltriethoxyphosphane ($C_9H_{21}N_3O_3P$), and an alkylphosphane or an alkylphosphonate.

In some additional, alternative, or selectively cumulative embodiments, a method of for making the pathogen-capturing material comprises: providing a fabric; and treating the fabric with a pathogen-binding chemical, wherein the pathogen-binding chemical comprises a multifunctional phosphane or a multifunctional phosphonate, including at least a first functional group and a second functional group, wherein the first functional group is configured to bond to the fabric and the second functional group is configured to bond to a protein-encapsulated airborne pathogen.

In some additional, alternative, or selectively cumulative embodiments, a method of for making the pathogen-capturing material comprises: providing a fabric; and treating the fabric with a pathogen-binding chemical, wherein the pathogen-binding chemical comprises a multifunctional phosphane or a multifunctional phosphonate, including at least a first functional group and a second functional group, wherein the first functional group is configured to bond to the fabric and the second functional group is configured to bond to a protein-encapsulated airborne pathogen, wherein the first functional group or second functional group comprises one or more of an amino group, an epoxy group, a carboxylate group, and an azide group which is configured to bond to a protein or a glycan on a protein-encapsulated airborne pathogen.

In some additional, alternative, or selectively cumulative embodiments, a method for capturing airborne pathogens comprises: providing a fabric treated with a pathogen-binding chemical, wherein the pathogen-binding chemical comprises a multifunctional phosphane or a multifunctional phosphonate having one or more of amino group, an epoxy group, a carboxylate group, and an azide group, any one of which is configured to covalently bond to a protein or a glycan on a protein-encapsulated airborne pathogen, wherein the fabric has opposing first and second sides; and causing air to sequentially pass through the first and second sides of the fabric; wherein prior to entering the first side of the fabric, the air has a measurable amount of protein-encapsulated airborne pathogens that are contagious to humans; wherein the amino group, the epoxy group, the carboxylate group, or the azide group of the pathogen-binding chemical of the fabric binds protein-encapsulated airborne pathogens flowing through the fabric; and wherein the air exiting the second side of the fabric contains no measurable amount of protein-encapsulated airborne pathogens that are contagious to humans.

In some additional, alternative, or selectively cumulative embodiments, a pathogen-capturing material for binding airborne pathogens, produced by a process comprising: providing a fabric; and treating the fabric with a pathogen-binding chemical, wherein the pathogen-binding chemical comprises a multifunctional phosphane or a multifunctional phosphonate, including at least a first functional group and a second functional group, wherein the first functional group is configured to bond to the fabric and the second functional group is configured to bond to a protein-encapsulated airborne pathogen, wherein the first functional group or second functional group comprises one or more of an amino group, an epoxy group, a carboxylate group, and an azide group which is configured to bond to a protein or a glycan on a protein-encapsulated airborne pathogen.

In some additional, alternative, or selectively cumulative embodiments, the pathogen-binding chemical comprises a multifunctional phosphane or a multifunctional phosphonate.

In some additional, alternative, or selectively cumulative embodiments, the pathogen-binding chemical comprises a bifunctional phosphane or a bifunctional phosphonate.

In some additional, alternative, or selectively cumulative embodiments, the pathogen-binding chemical comprises a trialkoxy phosphane or a trialkoxy phosphonate.

In some additional, alternative, or selectively cumulative embodiments, the pathogen-binding chemical comprises a multifunctional trialkoxy phosphane or a multifunctional trialkoxy phosphonate.

In some additional, alternative, or selectively cumulative embodiments, the pathogen-binding chemical comprises a bifunctional trialkoxy phosphane or phosphonate.

In some additional, alternative, or selectively cumulative embodiments, the pathogen-binding chemical comprises a triethoxy phosphane or a bifunctional trialkoxy phosphonate.

In some additional, alternative, or selectively cumulative embodiments, the pathogen-binding chemical comprises a multifunctional triethoxy phosphane or a multifunctional triethoxy phosphonate.

In some additional, alternative, or selectively cumulative embodiments, the pathogen-binding chemical comprises a bifunctional triethoxy phosphane or a bifunctional triethoxy phosphonate.

In some additional, alternative, or selectively cumulative embodiments, the pathogen-binding chemical comprises a multifunctional phosphane or a multifunctional phosphonate that includes a linker of 2 to 18 atoms between a phosphorous atom and one or more terminal functional groups.

In some additional, alternative, or selectively cumulative embodiments, the pathogen-binding chemical comprises a multifunctional phosphane or a multifunctional phosphonate that includes a linker of 2 to 12 atoms between a phosphorous atom and one or more terminal functional groups.

In some additional, alternative, or selectively cumulative embodiments, the pathogen-binding chemical comprises a multifunctional s phosphane or a multifunctional phosphonate that includes a linker of 2 to 8 atoms between a phosphorous atom and one or more terminal functional groups.

In some additional, alternative, or selectively cumulative embodiments, the pathogen-binding chemical comprises a multifunctional phosphane or a multifunctional phosphonate that includes an aliphatic linker of 2 to 18 atoms between a phosphorous atom and one or more terminal functional groups, and wherein atoms in the linker are predominately carbon.

In some additional, alternative, or selectively cumulative embodiments, the pathogen-binding chemical comprises a multifunctional phosphane or a multifunctional phosphonate that includes an aliphatic linker of 2 to 18 atoms between a phosphorous atom and one or more terminal functional groups, wherein atoms in the linker are predominately carbon, and wherein the linker contains one or more of oxygen, nitrogen, or sulfur.

In some additional, alternative, or selectively cumulative embodiments, the pathogen-binding chemical comprises a multifunctional phosphane or a multifunctional phosphonate that includes an aliphatic linker of 2 to 18 atoms between a phosphorous atom and one or more terminal functional groups, and the aliphatic linkers is flexible.

In some additional, alternative, or selectively cumulative embodiments, the pathogen-binding chemical comprises a multifunctional phosphane or a multifunctional phosphonate that includes an aliphatic linker of 2 to 18 atoms between a phosphorous atom and one or more terminal functional groups, and wherein the one or more of the terminal groups includes a simple amine.

In some additional, alternative, or selectively cumulative embodiments, the pathogen-binding chemical comprises a multifunctional phosphane or a multifunctional phosphonate that includes an aliphatic linker of 2 to 18 atoms between a phosphorous atom and one or more terminal functional groups, wherein the linker includes an internal simple amine, and wherein the one or more of the terminal groups includes a simple amine.

In some additional, alternative, or selectively cumulative embodiments, the pathogen-binding chemical comprises a multifunctional phosphane or a multifunctional phosphonate that includes an aliphatic linker of 2 to 18 atoms between a phosphorous atom and one or more terminal functional groups, wherein the linker includes a bis amine.

In some additional, alternative, or selectively cumulative embodiments, the pathogen-binding chemical comprises a multifunctional phosphane or a multifunctional phosphonate that includes an aliphatic linker of 2 to 18 atoms between a phosphorous atom and one or more terminal functional groups, wherein the linker includes a bis amine and a phenyl group.

In some additional, alternative, or selectively cumulative embodiments, the pathogen-binding chemical comprises a bifunctional phosphane or a bifunctional phosphonate having an organo-functional amino group configured to covalently bond a virus protein or a virus glycan.

In some additional, alternative, or selectively cumulative embodiments, the pathogen-binding chemical comprises a bifunctional phosphane or a bifunctional phosphonate having an epoxy group configured to covalently bond a virus protein or a virus glycan.

In some additional, alternative, or selectively cumulative embodiments, the pathogen-binding chemical comprises a multifunctional phosphane or a multifunctional phosphonate having an epoxy group configured to bond to one or more of an amine, a serine, a tyrosine, and a cysteine on the airborne pathogen.

In some additional, alternative, or selectively cumulative embodiments, the pathogen-binding chemical comprises a single phosphorous atom and a single linker.

In some additional, alternative, or selectively cumulative embodiments, the pathogen-binding chemical comprises an alkylphosphane or alkylphosphonate.

In some additional, alternative, or selectively cumulative embodiments, the pathogen-binding chemical comprises an aminophosphane or aminophosphonate.

In some additional, alternative, or selectively cumulative embodiments, the pathogen-binding chemical comprises 3-aminopropyltriethoxyphosphane ($C_9H_{23}NO_3P$).

In some additional, alternative, or selectively cumulative embodiments, the pathogen-binding chemical comprises (3-glycidoxypropyl)trimethoxyphosphane ($C_9H_{20}O_5P$).

In some additional, alternative, or selectively cumulative embodiments, the pathogen-binding chemical comprises N-(2-aminoethyl)-3-aminopropyltriethoxyphosphane ($C_{11}H_{28}N_2O_3P$).

In some additional, alternative, or selectively cumulative embodiments, the pathogen-binding chemical comprises 3-aminopropyltrimethoxyphosphane ($C_6H_{17}NO_3P$).

In some additional, alternative, or selectively cumulative embodiments, the pathogen-binding chemical comprises triethoxyphosphylpropylmaleamic acid ($C_{13}H_{25}NO_6P$).

In some additional, alternative, or selectively cumulative embodiments, the pathogen-binding chemical comprises (aminoethylaminomethyl)phenethyltrimethoxyphosphane ($C_{14}H_{26}N_2O_3P$).

In some additional, alternative, or selectively cumulative embodiments, the pathogen-binding chemical comprises 3-(N,N-dimethylaminopropyl)aminopropylmethyldimethoxyphosphane ($C_1H_{28}N_2O_2P$).

In some additional, alternative, or selectively cumulative embodiments, the pathogen-binding chemical comprises 3-azidopropyltriethoxyphosphane ($C_9H_{21}N_3O_3P$).

In some additional, alternative, or selectively cumulative embodiments, the fabric is configured in a form of a filter medium that is configured to allow air to pass therethrough, wherein the pathogen-binding chemical comprises one or more of 3-aminopropyltriethoxyphosphane ($C_9H_{23}NO_3P$), (3-glycidoxypropyl)trimethoxyphosphane ($C_9H_{20}O_5P$), N-(2-aminoethyl)-3-aminopropyltriethoxyphosphane ($C_{11}H_{28}N_2O_3P$), 3-aminopropyltrimethoxyphosphane ($C_6H_{17}NO_3P$), triethoxyphosphylpropylmaleamic acid ($C_{13}H_{25}NO_6P$), (aminoethylaminomethyl)phenethyltrimethoxyphosphane ($C_{14}H_{26}N_2O_3P$), 3-(N,N-dimethylaminopropyl)aminopropylmethyldimethoxyphosphane ($C_1H_{28}N_2O_2P$), and 3-azidopropyltriethoxyphosphlane ($C_9H_{21}N_3O_3P$), and an alkylphosphane or an alkylphosphonate.

In some additional, alternative, or selectively cumulative embodiments, the fabric comprises a filter, wherein the multifunctional chemical comprises a multifunctional phosphane or a multifunctional phosphonate, wherein the treated fabric has a coating of the pathogen-binding chemical with a depth of less than or equal to 5 nm, wherein more than or equal to 50% the pathogen-binding chemicals bound to the fabric are crosslinked to fewer than or equal to 5 of the same pathogen-binding chemicals, wherein the first functional group of the pathogen-binding chemical is bound to oxygen on the fabric, wherein the second functional group comprises one or more of an amino group, an epoxy group, a carboxylate group, and an azide group, and wherein the second functional is configured to bond to one or more of an amine, a serine, a tyrosine, and a cysteine on the airborne pathogen.

In some additional, alternative, or selectively cumulative embodiments, the fabric is configured in a form of a filter medium that is configured to allow air to pass therethrough, wherein the pathogen-binding chemical comprises one or more of 3-aminopropyltriethoxyphosphane ($C_9H_{23}NO_3P$), (3-glycidoxypropyl)trimethoxyphosphane ($C_9H_{20}O_5P$), N-(2-aminoethyl)-3-aminopropyltriethoxyphosphane ($C_1H_{28}N_2O_3Si$), 3-aminopropyltrimethoxyphosphane ($C_6H_{17}NO_3P$), triethoxyphosphylpropylmaleamic acid ($C_{13}H_{25}NO_6P$), (aminoethylaminomethyl)phenethyltrimethoxyphosphane ($C_{14}H_{26}N_2O_3P$), 3-(N,N-dimethylaminopropyl)aminopropylmethyldimethoxyphosphane ($C_1H_{28}N_2O_2P$), and 3-azidopropyltriethoxyphosphane ($C_9H_{21}N_3O_3P$), and an alkylphosphane or an alkylphosphonate.

In some additional, alternative, or selectively cumulative embodiments, the fabric is configured in a form of a wearable garment.

In some additional, alternative, or selectively cumulative embodiments, the fabric is configured in a form of personal protective equipment.

In some additional, alternative, or selectively cumulative embodiments, the personal protective equipment is one of surgical attire, an isolation gown, and a hazmat garment.

In some additional, alternative, or selectively cumulative embodiments, the fabric is configured in a form of a filter medium.

In some additional, alternative, or selectively cumulative embodiments, the filter medium is configured to allow air to pass therethrough.

In some additional, alternative, or selectively cumulative embodiments, the filter medium is configured for employment in an air circulation system.

In some additional, alternative, or selectively cumulative embodiments, the filter medium is one or more of a high-efficiency particulate air (HEPA) filter, a media filter, a spun-glass filter, and a pleated filter.

In some additional, alternative, or selectively cumulative embodiments, the filter medium comprises one or more of fiberglass, paper, cotton, polyester, metal, and carbon fiber.

In some additional, alternative, or selectively cumulative embodiments, the filter medium is configured in the form of a mask.

In some additional, alternative, or selectively cumulative embodiments, the filter is one of a surgical mask, a KN95 mask, an N95 mask, a surgical N95 mask, an N99 mask, an N100 mask, an R95 mask, a P95 mask, a P99 mask, and a P100 mask.

In some additional, alternative, or selectively cumulative embodiments, the filter in an untreated state has a MERV rating greater than or equal to 10.

In some additional, alternative, or selectively cumulative embodiments, the filter in an untreated state has a MERV rating greater than or equal to 12.

In some additional, alternative, or selectively cumulative embodiments, the filter in an untreated state has a MERV rating greater than or equal to 13.

In some additional, alternative, or selectively cumulative embodiments, the filter in a treated state has a MERV rating greater than or equal to 12.

In some additional, alternative, or selectively cumulative embodiments, the filter in a treated state has a MERV rating greater than or equal to 13.

In some additional, alternative, or selectively cumulative embodiments, the filter in a treated state has a MERV rating greater than or equal to 16.

In some additional, alternative, or selectively cumulative embodiments, the filter in a treated state has a MERV rating greater than or equal to 19.

In some additional, alternative, or selectively cumulative embodiments, the pathogen-binding chemical is configured to remove air-suspended virus from air.

In some additional, alternative, or selectively cumulative embodiments, the pathogen-binding chemical is nonbiologically produced.

In some additional, alternative, or selectively cumulative embodiments, the pathogen-binding chemical is synthetic.

In some additional, alternative, or selectively cumulative embodiments, the pathogen-binding chemical is nonmetallic.

In some additional, alternative, or selectively cumulative embodiments, the pathogen-binding chemical comprises a multifunctional silane.

In some additional, alternative, or selectively cumulative embodiments, the pathogen-binding chemical comprises a bifunctional silane.

In some additional, alternative, or selectively cumulative embodiments, the pathogen-binding chemical comprises a trialkoxy silane.

In some additional, alternative, or selectively cumulative embodiments, the pathogen-binding chemical comprises a multifunctional trialkoxy silane.

In some additional, alternative, or selectively cumulative embodiments, the pathogen-binding chemical comprises a bifunctional trialkoxy silane.

In some additional, alternative, or selectively cumulative embodiments, the pathogen-binding chemical comprises a triethoxy silane.

In some additional, alternative, or selectively cumulative embodiments, the pathogen-binding chemical comprises a multifunctional triethoxy silane.

In some additional, alternative, or selectively cumulative embodiments, the pathogen-binding chemical comprises a bifunctional triethoxy silane.

In some additional, alternative, or selectively cumulative embodiments, the pathogen-binding chemical comprises a multifunctional silane that includes a linker of 2 to 18 atoms between a silicon atom and one or more terminal functional groups.

In some additional, alternative, or selectively cumulative embodiments, the pathogen-binding chemical comprises a multifunctional silane that includes a linker of 2 to 12 atoms between a silicon atom and one or more terminal functional groups.

In some additional, alternative, or selectively cumulative embodiments, the pathogen-binding chemical comprises a multifunctional silane that includes a linker of 2 to 8 atoms between a silicon atom and one or more terminal functional groups.

In some additional, alternative, or selectively cumulative embodiments, the pathogen-binding chemical comprises a multifunctional silane that includes an aliphatic linker of 2 to 18 atoms between a silicon atom and one or more terminal functional groups, and wherein atoms in the linker are predominately carbon.

In some additional, alternative, or selectively cumulative embodiments, the pathogen-binding chemical comprises a multifunctional silane that includes an aliphatic linker of 2 to 18 atoms between a silicon atom and one or more terminal functional groups, wherein atoms in the linker are predominately carbon, and wherein the linker contains one or more of oxygen, nitrogen, or sulfur.

In some additional, alternative, or selectively cumulative embodiments, the pathogen-binding chemical comprises a multifunctional silane that includes an aliphatic linker of 2 to 18 atoms between a silicon atom and one or more terminal functional groups, and the aliphatic linkers is flexible.

In some additional, alternative, or selectively cumulative embodiments, the pathogen-binding chemical comprises a multifunctional silane that includes an aliphatic linker of 2 to 18 atoms between a silicon atom and one or more terminal functional groups, and wherein the one or more of the terminal groups includes a simple amine.

In some additional, alternative, or selectively cumulative embodiments, the pathogen-binding chemical comprises a multifunctional silane that includes an aliphatic linker of 2 to 18 atoms between a silicon atom and one or more terminal functional groups, wherein the linker includes an internal simple amine, and wherein the one or more of the terminal groups includes a simple amine.

In some additional, alternative, or selectively cumulative embodiments, the pathogen-binding chemical comprises a multifunctional silane that includes an aliphatic linker of 2 to 18 atoms between a silicon atom and one or more terminal functional groups, wherein the linker includes a bis amine.

In some additional, alternative, or selectively cumulative embodiments, the pathogen-binding chemical comprises a multifunctional silane that includes an aliphatic linker of 2 to 18 atoms between a silicon atom and one or more terminal functional groups, wherein the linker includes a bis amine and a phenyl group.

In some additional, alternative, or selectively cumulative embodiments, the pathogen-binding chemical comprises a bifunctional silane having an organo-functional amino group configured to covalently bond a virus protein or a virus glycan.

In some additional, alternative, or selectively cumulative embodiments, the pathogen-binding chemical comprises a bifunctional silane having an epoxy group configured to covalently bond a virus protein or a virus glycan.

In some additional, alternative, or selectively cumulative embodiments, the pathogen-binding chemical comprises a multifunctional silane having an epoxy group configured to bond to one or more of an amine, a serine, a tyrosine, and a cysteine on the airborne pathogen.

In some additional, alternative, or selectively cumulative embodiments, the pathogen-binding chemical is configured to bond to two or more of a virus, a bacteria, and a fungus.

In some additional, alternative, or selectively cumulative embodiments, the pathogen-binding chemical is configured to bond to two or more different viruses.

In some additional, alternative, or selectively cumulative embodiments, the pathogen-binding chemical is configured to bond to two or more different bacteria.

In some additional, alternative, or selectively cumulative embodiments, the pathogen-binding chemical is configured to bond to two or more different fungi.

In some additional, alternative, or selectively cumulative embodiments, the pathogen-binding chemical comprises a single silicon atom and a single linker.

In some additional, alternative, or selectively cumulative embodiments, the pathogen-binding chemical comprises an alkylsilane.

In some additional, alternative, or selectively cumulative embodiments, the pathogen-binding chemical comprises an aminosilane.

In some additional, alternative, or selectively cumulative embodiments, the pathogen-binding chemical comprises 3-aminopropyltriethoxysilane ($C_9H_{23}NO_3Si$).

In some additional, alternative, or selectively cumulative embodiments, the pathogen-binding chemical comprises (3-glycidoxypropyl)trimethoxysilane ($C_9H_{20}O_5Si$).

In some additional, alternative, or selectively cumulative embodiments, the pathogen-binding chemical comprises N-(2-aminoethyl)-3-aminopropyltriethoxysilane ($C_{11}H_{28}N_2O_3Si$).

In some additional, alternative, or selectively cumulative embodiments, the pathogen-binding chemical comprises 3-aminopropyltrimethoxysilane ($C_6H_{17}NO_3Si$).

In some additional, alternative, or selectively cumulative embodiments, the pathogen-binding chemical comprises triethoxysilylpropylmaleamic acid ($C_{13}H_{25}NO_6Si$).

In some additional, alternative, or selectively cumulative embodiments, the pathogen-binding chemical comprises (aminoethylaminomethyl)phenethyltrimethoxysilane ($C_{14}H_{26}N_2O_3Si$).

In some additional, alternative, or selectively cumulative embodiments, the pathogen-binding chemical comprises 3-(N,N-dimethylaminopropyl)aminopropylmethyldimethoxysilane ($C_{11}H_{28}N_2O_2Si$).

In some additional, alternative, or selectively cumulative embodiments, the pathogen-binding chemical comprises 3-azidopropyltriethoxysilane ($C_9H_{21}N_3O_3Si$).

In some additional, alternative, or selectively cumulative embodiments, the pathogen-binding chemical comprises a maleamic acid.

In some additional, alternative, or selectively cumulative embodiments, the pathogen-binding chemical comprises a calixarene.

In some additional, alternative, or selectively cumulative embodiments, the pathogen-binding chemical is covalently bonded to the fabric.

In some additional, alternative, or selectively cumulative embodiments, the the pathogen-binding chemical is covalently bonded to an oxygen atom on the fabric.

In some additional, alternative, or selectively cumulative embodiments, the pathogen-binding chemical bonds to the fabric exothermically.

In some additional, alternative, or selectively cumulative embodiments, the pathogen-binding chemical is configured to covalently bond to a virus.

In some additional, alternative, or selectively cumulative embodiments, the pathogen-binding chemical is configured to exothermically bond to a virus.

In some additional, alternative, or selectively cumulative embodiments, the pathogen-binding chemical is configured to bond to a spike protein of a virus.

In some additional, alternative, or selectively cumulative embodiments, the pathogen-binding chemical is configured to bond to a membrane protein of a virus.

In some additional, alternative, or selectively cumulative embodiments, the pathogen-binding chemical is configured to bond to an envelope protein of a virus.

In some additional, alternative, or selectively cumulative embodiments, the pathogen-binding chemical is configured to bond to a phospholipid bilayer of a virus.

In some additional, alternative, or selectively cumulative embodiments, the pathogen-binding chemical is configured to bond to multiple different viruses.

In some additional, alternative, or selectively cumulative embodiments, the pathogen-binding chemical is configured to bond to IgG.

In some additional, alternative, or selectively cumulative embodiments, the pathogen-binding chemical is configured to bond to human IgG.

In some additional, alternative, or selectively cumulative embodiments, the pathogen-binding chemical is configured to covalently bond to IgG.

In some additional, alternative, or selectively cumulative embodiments, the pathogen-binding chemical is configured to covalently bond to human IgG.

In some additional, alternative, or selectively cumulative embodiments, the pathogen-binding chemical is configured to bond to a virus of one or more of Adenoviridae, Anelloviridae, Arenaviridae, Astroviridae, Bornaviridae, Bunyaviridae, Caliciviridae, Coronaviridae, Filoviridae, Flaviviridae, Hepadnaviridae, Hepeviridae, Herpesviridae, Orthomyxoviridae, Papillomaviridae, Paramyxoviridae, Parvoviridae, Picobirnaviridae, Picornaviridae, Pneumoviridae, Polyomaviridae, Poxviridae, Reoviridae, Rhabdoviridae, and Togaviridae.

In some additional, alternative, or selectively cumulative embodiments, the pathogen-binding chemical is configured to bond to one or more of Adenovirus, Arenavirus, Coronavirus, Coxsackievirus, Echovirus, Filovirus, Monkeypox, Morbillivirus, Orthomyxovirus, Parainfluenza, Paramyxovirus, Parvovirus B19, Poxvirus, Reovirus, Respiratory Syncytial Virus, Rhinovirus, Togavirus, and Varicella.

In some additional, alternative, or selectively cumulative embodiments, the pathogen-binding chemical is configured to bond a phospholipid bilayer of a pathogenic bacteria.

In some additional, alternative, or selectively cumulative embodiments, the pathogen-binding chemical is configured to bond to a virus.

In some additional, alternative, or selectively cumulative embodiments, the the pathogen-binding chemical is configured to permanently bond to a virus.

In some additional, alternative, or selectively cumulative embodiments, the pathogen-binding chemical is configured to permanently bond to airborne pathogenic bacteria.

In some additional, alternative, or selectively cumulative embodiments, the pathogen-binding chemical is configured to permanently bond to oxygen atoms on the fabric.

In some additional, alternative, or selectively cumulative embodiments, the treated fabric has a coating of the pathogen-binding chemical with a depth of less than or equal to 10 nm.

In some additional, alternative, or selectively cumulative embodiments, the treated fabric has a coating of the pathogen-binding chemical with a depth of less than or equal to 5 nm.

In some additional, alternative, or selectively cumulative embodiments, the treated fabric has a coating of the pathogen-binding chemical with a depth of less than or equal to 2 nm.

In some additional, alternative, or selectively cumulative embodiments, the treated fabric has a coating of the pathogen-binding chemical with a depth of less than or equal to 1 nm.

In some additional, alternative, or selectively cumulative embodiments, the treated fabric has a coating of the pathogen-binding chemical with a depth of less than or equal to 0.5 nm.

In some additional, alternative, or selectively cumulative embodiments, the treated fabric has a coating of the pathogen-binding chemical with a depth in a range between 0.5 nm and 2 nm.

In some additional, alternative, or selectively cumulative embodiments, the treated fabric has a coating of the pathogen-binding chemical that is noncontiguous.

In some additional, alternative, or selectively cumulative embodiments, more than or equal to 50% the pathogen-binding chemicals bound to the fabric are crosslinked to fewer than or equal to 5 of the same pathogen-binding chemicals.

In some additional, alternative, or selectively cumulative embodiments, more than or equal to 75% the pathogen-binding chemicals bound to the fabric are crosslinked to fewer than or equal to 5 of the same pathogen-binding chemicals.

In some additional, alternative, or selectively cumulative embodiments, more than or equal to 90% the pathogen-binding chemicals bound to the fabric are crosslinked to fewer than or equal to 5 of the same pathogen-binding chemicals.

In some additional, alternative, or selectively cumulative embodiments, more than or equal to 50% the pathogen-binding chemicals bound to the fabric are crosslinked to fewer than or equal to 3 of the same pathogen-binding chemicals.

In some additional, alternative, or selectively cumulative embodiments, more than or equal to 75% the pathogen-binding chemicals bound to the fabric are crosslinked to fewer than or equal to 3 of the same pathogen-binding chemicals.

In some additional, alternative, or selectively cumulative embodiments, more than or equal to 90% the pathogen-binding chemicals bound to the fabric are crosslinked to fewer than or equal to 3 of the same pathogen-binding chemicals.

In some additional, alternative, or selectively cumulative embodiments, the fabric before and after treatment with the pathogen-binding chemical exhibits no difference in airflow as detected by a Retrotec DM32 manometer.

In some additional, alternative, or selectively cumulative embodiments, treatment of the fabric with the pathogen-binding chemical does not impede airflow through the fabric.

In some additional, alternative, or selectively cumulative embodiments, the fabric is configured in a form of a filter medium that is configured to allow air to pass therethrough, wherein the pathogen-binding chemical comprises a bifunctional silane having one or more of an organo-functional amino group and an epoxy group, either one of which is configured to covalently bond to a virus protein or a virus glycan.

In some additional, alternative, or selectively cumulative embodiments, treatment of the fabric with the pathogen-binding chemical results in non-toxic reaction biproducts below their toxicity threshold limit values (TLVs) to humans.

In some additional, alternative, or selectively cumulative embodiments, treatment of the fabric with the pathogen-binding chemical results in known reaction biproducts, wherein the known reaction biproducts are non-toxic to humans.

In some additional, alternative, or selectively cumulative embodiments, the fabric is configured in a form of a filter medium that is configured to allow air to pass therethrough, wherein the pathogen-binding chemical comprises one or more of 3-aminopropyltriethoxysilane ($C_9H_{23}NO_3Si$), (3-glycidoxypropyl)trimethoxysilane ($C_9H_{20}O_5Si$), N-(2-aminoethyl)-3-aminopropyltriethoxysilane ($C_{11}H_{28}N_2O_3Si$), 3-aminopropyltrimethoxysilane ($C_6H_{17}NO_3Si$), triethoxysilylpropylmaleamic acid ($C_{13}H_{25}NO_6Si$), (aminoethylaminomethyl)phenethyltrimethoxysilane ($C_{14}H_{26}N_2O_3Si$), 3-(N,N-dimethylaminopropyl)aminopropylmethyldimethoxysilane ($C_1H_{28}N_2O_2Si$), and 3-azidopropyltriethoxysilane ($C_9H_{21}N_3O_3Si$), maleamic acid, calixarene, and an alkylsilane.

In some additional, alternative, or selectively cumulative embodiments, the fabric comprises a filter, wherein the treated fabric has a coating of the pathogen-binding chemical with a depth of less than or equal to 5 nm, and wherein more than or equal to 50% the pathogen-binding chemicals bound to the fabric are crosslinked to fewer than or equal to 5 of the same pathogen-binding chemicals.

In some additional, alternative, or selectively cumulative embodiments, the fabric comprises a filter, wherein the treated fabric has a coating of the pathogen-binding chemical with a depth of less than or equal to 5 nm, wherein more than or equal to 50% the pathogen-binding chemicals bound to the fabric are crosslinked to fewer than or equal to 5 of the same pathogen-binding chemicals, and wherein the first functional group of the pathogen-binding chemical is bound to oxygen on the fabric.

In some additional, alternative, or selectively cumulative embodiments, the fabric comprises a filter, wherein the treated fabric has a coating of the pathogen-binding chemical with a depth of less than or equal to 5 nm, wherein more than or equal to 50% the pathogen-binding chemicals bound to the fabric are crosslinked to fewer than or equal to 5 of the same pathogen-binding chemicals, wherein the first functional group of the pathogen-binding chemical is bound to oxygen on the fabric, and wherein the second functional is configured to bond to one or more of an amine, a serine, a tyrosine, and a cysteine on the airborne pathogen.

In some additional, alternative, or selectively cumulative embodiments, the fabric comprises a filter, wherein the treated fabric has a coating of the pathogen-binding chemical with a depth of less than or equal to 5 nm, wherein more than or equal to 50% the pathogen-binding chemicals bound to the fabric are crosslinked to fewer than or equal to 5 of the same pathogen-binding chemicals, wherein the first functional group of the pathogen-binding chemical is bound to oxygen on the fabric, wherein the second functional group comprises one or more of an amino group, an epoxy group, a carboxylate group, and an azide group, and wherein the second functional is configured to bond to one or more of an amine, a serine, a tyrosine, and a cysteine on the airborne pathogen.

In some additional, alternative, or selectively cumulative embodiments, the fabric comprises a filter, wherein the multifunctional chemical comprises a multifunctional silane, wherein the treated fabric has a coating of the pathogen-binding chemical with a depth of less than or equal to 5 nm, wherein more than or equal to 50% the pathogen-binding chemicals bound to the fabric are crosslinked to fewer than or equal to 5 of the same pathogen-binding chemicals, wherein the first functional group of the pathogen-binding chemical is bound to oxygen on the fabric, wherein the second functional group comprises one or more of an amino group, an epoxy group, a carboxylate group, and an azide group, and wherein the second functional is configured to bond to one or more of an amine, a serine, a tyrosine, and a cysteine on the airborne pathogen.

In some additional, alternative, or selectively cumulative embodiments, the first functional group or second functional group comprises one or more of an amino group, an epoxy group, a carboxylate group, and an azide group which is configured to bond to a protein or a glycan on a protein-encapsulated airborne pathogen.

In some additional, alternative, or selectively cumulative embodiments, treating the fabric employs a plasma treatment with the pathogen-binding chemical.

In some additional, alternative, or selectively cumulative embodiments, treating the fabric employs a corona discharge-like treatment with the pathogen-binding chemical.

In some additional, alternative, or selectively cumulative embodiments, the fabric is treated in a chemical vapor deposition (CVD) chamber.

In some additional, alternative, or selectively cumulative embodiments, the fabric is treated in a plasma-enhanced chemical vapor deposition (PECVD) chamber.

In some additional, alternative, or selectively cumulative embodiments, the fabric is moved into a chemical vapor deposition (CVD) chamber, and the pathogen-binding chemical is preheated before treating the fabric.

In some additional, alternative, or selectively cumulative embodiments, the fabric is moved into a chemical vapor deposition (CVD) chamber; the fabric is pretreated with oxygen and optionally subsequently pretreated with water or an alcohol; and the pathogen-binding chemical is preheated before treating the fabric.

In some additional, alternative, or selectively cumulative embodiments, the fabric is subjected to a plasma pretreatment step with one or more of oxygen, water, and an alcohol before treating the fabric.

In some additional, alternative, or selectively cumulative embodiments, the fabric is moved into a chemical vapor deposition (CVD) chamber; the fabric is subjected to a plasma pretreatment step with one or more of oxygen, water, and an alcohol; and the pathogen-binding chemical is preheated before treating the fabric.

In some additional, alternative, or selectively cumulative embodiments, the fabric is pretreated with one or more of oxygen, water, and an alcohol.

In some additional, alternative, or selectively cumulative embodiments, the fabric is pretreated with oxygen and subsequently pretreated with water or an alcohol.

In some additional, alternative, or selectively cumulative embodiments, pretreatment chemicals are applied low-pressure glow discharge.

In some additional, alternative, or selectively cumulative embodiments, the pathogen-binding chemical is applied to the fabric in a sub-atmospheric gas-phase flow-through reactor.

In some additional, alternative, or selectively cumulative embodiments, the pathogen-binding chemical is applied to the fabric at a temperature greater than or equal to 25° C.

In some additional, alternative, or selectively cumulative embodiments, the pathogen-binding chemical is applied to the fabric at a temperature greater than or equal to 40° C.

In some additional, alternative, or selectively cumulative embodiments, the pathogen-binding chemical is applied to the fabric at a temperature less than or equal to 150° C.

In some additional, alternative, or selectively cumulative embodiments, the pathogen-binding chemical is applied to the fabric at a temperature less than or equal to 125° C.

In some additional, alternative, or selectively cumulative embodiments, the pathogen-binding chemical is applied to the fabric at a temperature less than or equal to 100° C.

In some additional, alternative, or selectively cumulative embodiments, the pathogen-binding chemical is applied to the fabric at a temperature less than or equal to 80° C.

In some additional, alternative, or selectively cumulative embodiments, the pathogen-binding chemical is applied to the fabric at a temperature less than or equal to 70° C.

In some additional, alternative, or selectively cumulative embodiments, the pathogen-binding chemical is applied to the fabric at a temperature greater than or equal to 40° C. and less than or equal to 150° C.

In some additional, alternative, or selectively cumulative embodiments, the pathogen-binding chemical is applied to the fabric at a pressure less than or equal to 6666 Pa.

In some additional, alternative, or selectively cumulative embodiments, the pathogen-binding chemical is applied to the fabric at a pressure less than or equal to 3333 Pa.

In some additional, alternative, or selectively cumulative embodiments, the pathogen-binding chemical is applied to the fabric at a pressure less than or equal to 1000 Pa.

In some additional, alternative, or selectively cumulative embodiments, the pathogen-binding chemical is applied to the fabric at a pressure less than or equal to 500 Pa.

In some additional, alternative, or selectively cumulative embodiments, the pathogen-binding chemical is applied to the fabric at a pressure less than or equal to 133 Pa.

In some additional, alternative, or selectively cumulative embodiments, the pathogen-binding chemical is applied to the fabric at a pressure greater than or equal to 1 Pa.

In some additional, alternative, or selectively cumulative embodiments, the pathogen-binding chemical is applied to the fabric at a pressure greater than or equal to 10 Pa.

In some additional, alternative, or selectively cumulative embodiments, the pathogen-binding chemical is applied to the fabric at a pressure greater than or equal to 10 Pa and less than or 133 Pa.

In some additional, alternative, or selectively cumulative embodiments, a pretreatment chemical is applied to the fabric at a temperature greater than or equal to 25° C.

In some additional, alternative, or selectively cumulative embodiments, a pretreatment chemical is applied to the fabric at a temperature greater than or equal to 40° C.

In some additional, alternative, or selectively cumulative embodiments, a pretreatment chemical is applied to the fabric at a temperature less than or equal to 150° C.

In some additional, alternative, or selectively cumulative embodiments, a pretreatment chemical is applied to the fabric at a temperature less than or equal to 125° C.

In some additional, alternative, or selectively cumulative embodiments, a pretreatment chemical is applied to the fabric at a temperature less than or equal to 100° C.

In some additional, alternative, or selectively cumulative embodiments, a pretreatment chemical is applied to the fabric at a temperature less than or equal to 80° C.

In some additional, alternative, or selectively cumulative embodiments, a pretreatment chemical is applied to the fabric at a temperature less than or equal to 70° C.

In some additional, alternative, or selectively cumulative embodiments, a pretreatment chemical is applied to the fabric at a temperature greater than or equal to 40° C. and less than or equal to 150° C.

In some additional, alternative, or selectively cumulative embodiments, a pretreatment chemical is applied to the fabric at a pressure less than or equal to 6666 Pa.

In some additional, alternative, or selectively cumulative embodiments, a pretreatment chemical is applied to the fabric at a pressure less than or equal to 3333 Pa.

In some additional, alternative, or selectively cumulative embodiments, a pretreatment chemical is applied to the fabric at a pressure less than or equal to 1000 Pa.

In some additional, alternative, or selectively cumulative embodiments, a pretreatment chemical is applied to the fabric at a pressure less than or equal to 500 Pa.

In some additional, alternative, or selectively cumulative embodiments, a pretreatment chemical is applied to the fabric at a pressure less than or equal to 133 Pa.

In some additional, alternative, or selectively cumulative embodiments, a pretreatment chemical is applied to the fabric at a pressure greater than or equal to 1 Pa.

In some additional, alternative, or selectively cumulative embodiments, a pretreatment chemical is applied to the fabric at a pressure greater than or equal to 10 Pa.

In some additional, alternative, or selectively cumulative embodiments, a pretreatment chemical is applied to the fabric at a pressure greater than or equal to 10 Pa and less than or 133 Pa.

In some additional, alternative, or selectively cumulative embodiments, the pathogen-binding chemical is applied to the fabric in a treatment of less than or equal to 1 hour.

In some additional, alternative, or selectively cumulative embodiments, the pathogen-binding chemical is applied to the fabric in a treatment of less than or equal 45 minutes.

In some additional, alternative, or selectively cumulative embodiments, the pathogen-binding chemical is applied to the fabric in a treatment of less than or equal 30 minutes.

In some additional, alternative, or selectively cumulative embodiments, the fabric is configured in a form of a filter medium that is configured to allow air to pass therethrough, wherein the pathogen-binding chemical comprises one or more of 3-aminopropyltriethoxysilane ($C_9H_{23}NO_3Si$), (3-glycidoxypropyl)trimethoxysilane ($C_9H_{20}O_5Si$), N-(2-aminoethyl)-3-aminopropyltriethoxysilane ($C_{11}H_{28}N_2O_3Si$), 3-aminopropyltrimethoxysilane ($C_6H_{17}NO_3Si$), triethoxysilylpropylmaleamic acid ($C_{13}H_{25}NO_6Si$), (aminoethylaminomethyl)phenethyltrimethoxysilane ($C_{14}H_{26}N_2O_3Si$), 3-(N,N-dimethylaminopropyl)aminopropylmethyldimethoxysilane ($C_{11}H_{28}N_2O_2Si$), and 3-azidopropyltriethoxysilane ($C_9H_{21}N_3O_3Si$), maleamic acid, calixarene, and an alkylsilane.

In some additional, alternative, or selectively cumulative embodiments, treating the fabric with a pathogen-binding chemical results in non-toxic reaction biproducts below their threshold limit values (TLVs) to humans.

In some additional, alternative, or selectively cumulative embodiments, treating the fabric with a pathogen-binding chemical results in known reaction biproducts, wherein the known reaction biproducts are non-toxic to humans.

Selectively cumulative embodiments are embodiments that include any combination of multiple embodiments that are not mutually exclusive.

Additional aspects and advantages will be apparent from the following detailed description of example embodiments, which proceeds with reference to the accompanying drawings.

BRIEF DESCRIPTION OF THE DRAWINGS

FIG. 1A is a pictorial illustration, showing an airstream containing pathogens passing through an untreated prior art filter that allows the pathogens to pass through it.

FIG. 1B is a pictorial illustration, showing a treated filter binding pathogens and preventing their propagation through the filter.

FIGS. 2A-2C present respective Tables 1A-1C that show examples of chemicals that can be used in coatings to bind pathogens.

FIG. 5 is a bar graph showing the relative binding of SARS-CoV-2 spike protein applied at different concentrations to microtiter plates treated with a different one of three of the bifunctional silane chemicals listed in Tables 1A-1C.

FIG. 6 is a bar graph showing the relative binding of SARS-CoV-2 spike protein applied at different concentrations to microtiter plates treated with a different one of four other of the bifunctional silane chemicals listed in Tables 1A-1C.

FIGS. 8A-8C present respective Tables 2A-2C that show examples of additional chemicals that can be used in coatings to bind pathogens.

DETAILED DESCRIPTION OF EMBODIMENTS

Figure 3:
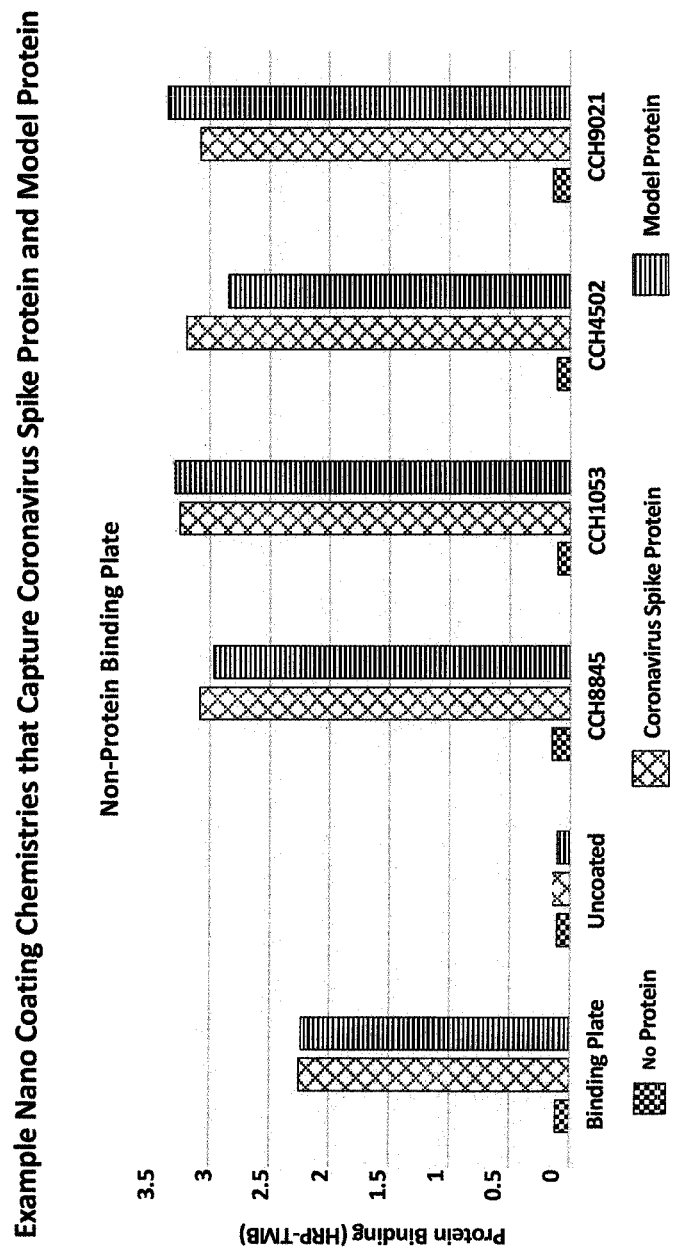
FIG. 3 is bar graph showing the relative binding of SARS-CoV-2 spike protein and IgG applied independently in fixed concentrations to control plates and microtiter plates treated with a different one four bifunctional silane chemicals listed in Tables 1A-1C.

Example embodiments are described below with reference to the accompanying drawings. Unless otherwise expressly stated in the drawings, the sizes, positions, etc., of components, features, elements, etc., as well as any distances therebetween, are not necessarily to scale, and may be disproportionate and/or exaggerated for clarity.

The terminology used herein is for the purpose of describing particular example embodiments only and is not intended to be limiting. As used herein, the singular forms "a," "an" and "the" are intended to include the plural forms as well, unless the context clearly indicates otherwise. It should be recognized that the terms "comprise," "comprises," "comprising," "includes," "include," "including," "have," "has," and having" when used in this specification, specify the presence of stated features, integers, steps, operations, elements, and/or components, but do not preclude the presence or addition of one or more other features, integers, steps, operations, elements, components, and/or groups thereof. Unless otherwise specified, a range of values, when recited, includes both the upper and lower limits of the range, as well as any sub-ranges therebetween. Unless indicated otherwise, terms such as "first," "second," etc., are only used to distinguish one element from another. For example, one element could be termed a "first element" and similarly, another element could be termed a "second element," or vice versa. The section headings used herein are for organizational purposes only and are not to be construed as limiting the subject matter described.

Unless indicated otherwise, the terms "about," "thereabout," "substantially," etc. mean that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art.

Spatially relative terms, such as "right," left," "below," "beneath," "lower," "above," and "upper," and the like, may be used herein for ease of description to describe one element's or feature's relationship to another element or feature, as illustrated in the drawings. It should be recognized that the spatially relative terms are intended to encompass different orientations in addition to the orientation depicted in the figures. For example, if an object in the figures is turned over, elements described as "below" or "beneath" other elements or features would then be oriented "above" the other elements or features. Thus, the exemplary term "below" can, for example, encompass both an orientation of above and below. An object may be otherwise oriented (e.g., rotated 90 degrees or at other orientations) and the spatially relative descriptors used herein may be interpreted accordingly.

Unless clearly indicated otherwise, all connections and all operative connections may be direct or indirect. Similarly, unless clearly indicated otherwise, all connections and all operative connections may be rigid or non-rigid.

Like numbers refer to like elements throughout. Thus, the same or similar numbers may be described with reference to other drawings even if they are neither mentioned nor described in the corresponding drawing. Also, even elements that are not denoted by reference numbers may be described with reference to other drawings.

Many different forms and embodiments are possible without deviating from the spirit and teachings of this disclosure and so this disclosure should not be construed as limited to the example embodiments set forth herein. For example, pathogens are largely discussed herein by way of example to viruses; however, one will appreciate that the techniques disclosed herein can be applied to bacteria as well.

The spread of SARS-CoV-2 pandemic has been attributed to airborne respiratory droplets. Droplets are considered large respiratory particles, typically 5 to 10 μm in size, which serve as virus carriers that are expelled when an infected person coughs, sneezes, or simply speaks. However, submicron size (<1 μm) droplets can linger in the air for greater distances and can even stay aloft for long periods of time. These droplets can carry the infectious virus and other pathogens. Current masks, filters, respirators and a variety of similar products that are supposed to prevent users from inhaling hazardous droplets/particles can be ineffective. At most, these products provide a barrier to these pathogens. However, some microscopic particles bounce around in zigzag patterns within these conventional products and are not captured by them.

Many viruses and other pathogens that are trapped in a filter can stay there and eventually "die" without further harmful effects. However, some viruses (similar to SARS-CoV-2) can live for up to three days on surfaces and are inefficiently trapped. These types of viruses can make filters, masks and respirators ineffective in combating serious airborne viruses. Moreover, when people handle used PPEs and other filters for replacement or disposal, the pathogens can be re-aerosolized, greatly increasing the risk of infection. FIG. 1A is a pictorial illustration, showing an airstream 10 containing pathogens 12 passing through untreated prior art filter 14 (or other untreated prior art PPE fabric) that allows the pathogens 12 to pass through it. The filter 14 may be capable of capturing some pathogens based on mechanical aspects of the filter 14, such pore size, but airborne pathogens 12, such as viruses and bacteria can pass through the filter 14.

Viruses are composed of nucleic acid (DNA or RNA) packaged within a phospholipid bilayer obtained from the host cell upon exiting the cell. This phospholipid bilayer contains specific proteins that facilitate entry into a target cell. Together, the protein-rich phospholipid bilayer constitutes the viral "coat," i.e., a virus is a protein-encapsulated pathogen. The scientific community has developed a detailed understanding of the specific structure and composition of the viral coats of most common viruses.

For example, the novel coronavirus SARS-CoV-2 (which causes COVID-19) contains multiple proteins in the phospholipid bilayer on the viral particle surface, all of which have been sequenced and characterized. These encapsulating proteins include: the spike protein (involved in host cell infectivity), the membrane protein (facilitating the structural integrity of the viral particle), and the envelope protein (facilitating structural integrity of the viral coat). Each of these proteins provides unique opportunities for viral capture based on structure or charge.

These proteins can also be targeted for viral capture by taking advantage of known post-translational modifications that occur after the proteins are initially synthesized by a virus. The envelope protein, for example, is post-translationally modified via palmitoylation (the covalent attachment of fatty acids to cysteine residues found on the outside of the viral membrane), providing additional opportunities for viral capture. Finally, viral particles can be captured based on the negative charge intrinsic to phospholipids.

One will appreciate that bacterial pathogens are also encapsulated by a phospholipid layer that is densely populated with protein, i.e., bacteria can also be a protein-encapsulated pathogen. One will also appreciate that fungal pathogens are also encapsulated by a phospholipid layer that is densely populated with protein, i.e., fungi can also be a protein-encapsulated pathogen. Finally, one will further appreciate that that the pathogen need not be an infectious pathogen. A pathogen may be simply be an allergen, such as allergens that are protein encapsulated. Moreover, some fungi cause allergies without causing infection.

By finding agents such as chemicals that bind to one or more of these proteins or to the phospholipid in the pathogen protein-encapsulating coat and developing these chemicals into coatings that can be applied to fabrics (such as in the forms of filtration media or garments), the applicants have developed an improved pathogen-capture system that can be used in the contexts of filtration and/or purification systems and PPE apparel. Moreover, these chemicals were selected to have a reactive end group that can be attached to the fabrics and a functional component with the desired pathogen-binding properties to impart to fabrics.

Specialized techniques have also been developed to facilitate application of the selected chemicals to the fabrics. Some of these techniques involve depositing a layer of one or more molten or semi-molten chemicals onto a fabric. These techniques can make products that can permanently entrap particulate matters including pathogens, such as harmful viruses and/or bacteria, and greatly improve the efficacy of masks, respirators, filters, garments, PPE, and other products for reducing airborne transmission of disease. FIG. 1B is a pictorial illustration, showing a treated filter 20 (or other PPE fabric) that bonds or chemically immobilizes pathogens 12 and prevents their propagation through the treated filter 20 so that the airstream 10 is substantially devoid of pathogens.

Moieties were considered that could bond to fabrics and/or exposed pathogen functional groups, such as proteins and/or glycans. Fabrics include woven and nonwoven material as well as natural or synthetic materials. For purposes of this disclosure, fabrics do not include materials that are solid and inflexible at typical ambient temperatures, such as glass or polystyrene plates. A fabric may include materials employed for, or configured as, a filter medium, a garment, or any type of PPE.

Filter media may include any type of material that is configured to allow air to pass through it, such as a fibrous or porous material. Examples of filter media include, but are not limited to, fiberglass, paper, cotton, polyester, metal, carbon fiber, combinations thereof, or other pliable materials. Filters may be configured as HEPA or nonHEPA filters. The filter may have a MERV rating that is greater than or equal to 10, greater than or equal to 12, greater than or equal to 13, greater than or equal to 16, or greater than or equal to 19. Alternatively, the filter may have a MERV rating that is less than or equal to 22, less than or equal to 19, less than or equal to 17, less than or equal to 15, less than or equal to 12, or less than or equal to 10. One will appreciate that the MERV rating may be in a range between any of these values.

The filter may be configured to form a face mask, such as one of a surgical mask, a KN95 mask, an N95 mask, a surgical N95 mask, an N99 mask, an N100 mask, an R95 mask, a P95 mask, a P99 mask, and a P100 mask. Alternatively, the filter may be configured to serve in air filtration or air purification systems, such as for hospitals, airlines, clean rooms, buildings, public spaces, schools, places of worship, churches, mosques, synagogues, temples, hotel rooms, cruise line cabins, athletic gyms, restaurants, and homes.

Garments may include any type of apparel including, but not limited to, gowns, hair coverings, gloves, booties, protective eye wear, white coats, lab coats, scrubs, etc. One will appreciate that many garments can be classified as PPE item, and that facemasks can be classified as either a garment or PPE item, as well as a filter.

The pathogen-binding agents may be nonbiologically produced or derived. Moreover, the pathogen-binding agents may be synthetic chemicals, such as those that could be readily employed in a manufacturing process. The pathogen-binding chemicals, themselves, may be non-toxic to humans or may be used in concentration below their toxicity threshold limit values (TLVs) to humans. In this regard, the pathogen-binding chemicals may be nonmetallic. Moreover, treatment of the fabrics with the pathogen-binding chemicals may result in known reaction biproducts that are non-toxic to humans or result in known reaction biproducts below their toxicity threshold limit values (TLVs) to humans.

However, some chemicals deemed toxic to humans may be employed. For examples, toxic chemicals that irreversibly bond to fabrics may be applied to an area of fabric that does not come into contact with humans. For example, such chemicals may be applied to remote system filters or to noncontactable areas of a PPE item.

The pathogen-binding chemical may covalently bond to one or more of the fabrics and, more particularly, may bond to the fabric in an endothermic reaction, an exothermic reaction, or an irreversible reaction. Similarly, the pathogen-binding chemical may covalently bond to one or more of a virus, bacteria, fungus, and human immunoglobulin G (IgG) and, more particularly, may bond to one or more of a virus, bacteria, fungus, and human IgG in an endothermic reaction, an exothermic reaction, or an irreversible reaction. Moreover, the pathogen-binding chemical may covalently bond to multiple different viruses, bacteria, and fungi and, more particularly, may bond to multiple different viruses, bacteria, and fungi in an endothermic reaction, an exothermic reaction, or an irreversible reaction.

The pathogen-binding chemical may covalently (or noncovalently) bond to a protein coat of one or more of a virus, bacteria, and fungus and, more particularly, may bond to a protein coat of one or more of a virus, bacteria, and fungus, in an endothermic reaction, an exothermic reaction, or an irreversible reaction. Moreover, the pathogen-binding chemical may covalently (or noncovalently) bond to the proteins and/or glycans of one or more of an airborne protein-encapsulated virus, fungus, and bacteria and, more particularly, may bond to the proteins and/or glycans of one or more of an airborne protein-encapsulated virus, bacteria, and fungus, in an endothermic reaction, an exothermic reaction, or an irreversible reaction.

The pathogen-binding chemical may covalently (or noncovalently) bond to a phospholipid bilayer of a pathogen and, more particularly, may bond to a phospholipid bilayer of pathogen in an endothermic reaction, an exothermic reaction, or an irreversible reaction. The pathogen-binding chemical may covalently (or noncovalently) bond to phospholipid bilayer of bacteria and, more particularly, may bond to phospholipid bilayer of bacteria in an endothermic reaction, an exothermic reaction, or an irreversible reaction. The pathogen-binding chemical may covalently (or noncovalently) bond to phospholipid bilayer of a fungus and, more particularly, may bond to phospholipid bilayer of a fungus in an endothermic reaction, an exothermic reaction, or an irreversible reaction.

The pathogen-binding chemical may covalently (or noncovalently) bond to phospholipid bilayer of a virus and, more particularly, may bond to phospholipid bilayer of a virus in an endothermic reaction, an exothermic reaction, or an irreversible reaction. Moreover, the pathogen-binding chemical may covalently (or noncovalently) bond to one or more of a spike protein, membrane protein, and envelope protein of a virus and, more particularly, may bond to one or more of spike protein, membrane protein, and envelope protein of a virus in an endothermic reaction, an exothermic reaction, or an irreversible reaction.

The pathogen-binding chemical may bind to a virus of one or more of Adenoviridae, Anelloviridae, Arenaviridae, Astroviridae, Bornaviridae, Bunyaviridae, Caliciviridae, Coronaviridae, Filoviridae, Flaviviridae, Hepadnaviridae, Hepeviridae, Herpesviridae, Orthomyxoviridae, Papillomaviridae, Paramyxoviridae, Parvoviridae, Picobirnaviridae, Picornaviridae, Pneumoviridae, Polyomaviridae, Poxviridae, Reoviridae, Rhabdoviridae, and Togaviridae and, more particularly, may bond to one or more of these viruses in an endothermic reaction, an exothermic reaction, or an irreversible reaction. Alternatively, the pathogen-binding chemical may bind to one or more of Adenovirus, Arenavirus, Coronavirus, Coxsackievirus, Echovirus, Filovirus, Influenza virus, Monkeypox virus, Morbillivirus, Orthomyxovirus, Parainfluenza, Paramyxovirus, Parvovirus B19, Poxvirus, Reovirus, Respiratory Syncytial Virus, Rhinovirus, Togavirus, and Varicella virus and, more particularly, may bond to one or more of these viruses in an endothermic reaction, an exothermic reaction, or an irreversible reaction.

The pathogen-binding chemical may bind to one or more bacteria, such as in an endothermic reaction, an exothermic reaction, or an irreversible reaction. The bacteria may be one or more of, but not limited to, *Acinetobacter, Actinomyces israelii, Alkaligenes, Bacillus anthracis, Bordetella pertussis, Cardiobacterium, Chlamydia pneumoniae, Chlamydia psittaci, Clostridium tetani, Corynebacteria diphtheria, Coxiella burnetiid, Enterobacter cloacae, Enterococcus, Francisella tularensis, Haemophilus influenzae, Haemophilus parainfluenzae, Klebsiella pneumoniae, Legionella parisiensis, Legionella pneumophila, Moraxella catarrhalis, Moraxella lacunata, Mycobacterium kansasii, Mycobacterium avium, Mycobacterium intracellulare, Mycobacterium tuberculosis, Mycoplasma pneumoniae, Neisseria meningitidis, Pseudomonas aeruginosa, Pseudomonas cepacian, Pseudomonas mallei, Pseudomonas pseudomallei, Serratia marcescens, Staphylococcus aureus, Staphylococcus epidermis, Streptococcus faecalis, Streptococcus pneumoniae, Streptococcus pyogenes*, and *Yersinia pestis*.

The pathogen-binding chemical may bind to one or more fungi, such as in an endothermic reaction, an exothermic reaction, or an irreversible reaction. The fungi may be one or more of, but not limited to, *Absidia corymbifera, Acremonium* spp., *Alternaria Aureobasidium pullulans, Blastomyces dermatitidis, Botrytis cinera, Candida albicans, Chaetomium globosum, Cladosporium cladosporioides, Cladosporium herbarum, Cladosporium sphaerospermum, Coccidioides immitis, Cryptococcus albidus, Cryptococcus laurentii, Cryptococcus neoformans, Emericella nidulans, Epicoccum nigrum, Eurotium amstelodami, Eurotium herbariorum, Eurotium rubrum, Exophiala jeanselmei, Fusarium culmorum, Fusarium graminearum, Fusarium moniliforme, Fusarium solani, Fusarium sporotrichioides, Geomyces pannorum, Helminthosporium, Histoplasma capsulatum, Mucor plumbeus, Oidiodendron tenuissimum, Paecilomyces variotii, Paracoccidioides brasiliensis, Penicillium brevicompactum, Penicillium chrysogenum, Penicillium citreonigrum, Penicillium commune, Penicillium corylophilum, Penicillium cyclopium, Penicillium expansum, Penicillium freii, Penicillium glabrum, Penicillium hordei, Penicillium olsonii, Penicillium polonicum, Penicillium rugulosum, Penicillium solitum, Phialaphora hoffmannii, Phialaphora mutabilis, Phialaphora parasitica, Phialaphora repens, Phialaphora richardsiae, Phoma* spp., *Rhizomucor pusillus, Rhizopus stolonifera, Rhodoturula glutinous, Rhodoturula minuta, Rhodoturula mucilaginosa, Scopulariopsis brevicaulis, Scopulariopsis fusca, Sporothrix schenckii, Stachybotris atra, Stachybotris chartarum, Trichoderma harzianum, Trichoderma viride, Ulocladium botrytis, Ulocladium chartarum,* and *Wallemia sebi*.

Pathogen-binding agents that may be applied as coatings for fabrics may include moieties with bio-reactive functional groups. These pathogen-binding agents include multifunctional (including bifunctional) molecules. Some of the functional groups may be configured to have an affinity to bond to the fabrics, either generically or with individualized selectivity. For example, functional groups that have an affinity to bond with exposed oxygen groups on the fabrics may be selected. In some embodiments, silane functional groups may be selected.

Functional groups that may facilitate binding to pathogen proteins may include, but are not limited to, amino groups, epoxy groups, carboxyl groups, aldehyde groups, and sulfur groups, and any combination thereof. The amino groups may bind noncovalently to negative charges on protein. The epoxy groups may facilitate covalent binding to amine, serine, and tyrosine on the pathogen proteins. A carboxyl group may react covalently with amines on the pathogen protein, and a C=C double bond may react covalently with amine groups on the pathogen protein.

The pathogen-binding agents may include multifunctional (including bifunctional) silanes with organo-functional amino and/or epoxy groups that can robustly or covalently bond to the fabrics and to the proteins and/or glycans of a protein-encapsulated airborne pathogen. Some examples of useful silane functional groups include, but are not limited to, dimethylamine, hydrogen chloride, silazane, methoxy, and ethoxy. Moreover, multifunctional silanes that are useful as pathogen-binding agents for fabric coatings may include, but are not limited to, include trialkoxy silanes, such as trimethoxy silanes and triethoxy silanes.

Additionally, multifunctional silanes that are useful as pathogen-binding agents for fabric coatings may have, for example, linker(s) of 2 to 18 atoms between the fabric surface attachment point or nearest silane functional group and one or more of a variety of terminal functional groups at the other end of the linking chain. In some embodiments, the linker(s) may have 2 to 12 or 2 to 8 atoms between the fabric surface attachment point or nearest silane functional group and one or more of a variety of terminal functional groups at the other end of the linking chain.

In some embodiments, multifunctional silanes that are useful as pathogen-binding agents for fabric coatings may have, for example, linker(s) of 2 to 18 atoms between the silicon atom and one or more of a variety of terminal functional groups at the other end of the linking chain. In some embodiments, the linker(s) may have 2 to 12 or 2 to 8 atoms between the silicon atom and one or more of a variety of terminal functional groups at the other end of the linking chain.

In many embodiments, the linkers may be aliphatic linking chains. Thus, the atoms in these linkers may be predominately carbon, but the linker may also contain one or more of oxygen, nitrogen, or sulfur. The aliphatic linkers may be flexible as the flexibility of these linkers may be configured by manipulating the number of carbon atoms and the types and numbers of noncarbon atoms. One will appreciate that the aliphatic linker may have more than 18 atoms or that the linker may be nonaliphatic.

Additionally, flexible aliphatic linkers containing an amine, such as a simple amine, at the terminal end may be useful for binding exposed pathogen proteins. Linkers that contain both a basic internal amine within the linker and at its terminal end may be particularly useful for binding exposed pathogen proteins. Without being held to any particular theory, it is believed that the amine linkers presumably are cationic in nature and presumably, but not necessarily, bind to the exposed negatively charged (anionic) protein residues of the airborne pathogens.

In some embodiments, the linker may be a bis amine linker. In particular, the bis amine linker may include a phenyl group that may add hydrophobicity to the linker. Without being held to any particular theory, it is believed that such a linker may have hydrophobic and polar cationic amine entities that may provide additive effects in binding to the proteins of airborne pathogens. The phenyl group may also add an element of rigidity to the linker. Without being held to any particular theory, it is believed that rigidity may help pre-organize the linker towards binding and thus increase binding efficiency. In some embodiments, the linker may include a terminal azide functional group.

Examples of specific multifunctional silanes that may be employed as pathogen-binding chemicals include, but are not limited to, (3-glycidoxypropyl)trimethoxysilane ($C_9H_{20}O_5Si$), N-(2-aminoethyl)-3-aminopropyltriethoxysilane ($C_{11}H_{28}N_2O_3Si$), 3-aminopropyltrimethoxysilane ($C_6H_{17}NO_3Si$), triethoxysilylpropylmaleamic acid ($C_{13}H_{25}NO_6Si$), (aminoethylaminomethyl)phenethyltrimethoxysilane ($C_{14}H_{26}N_2O_3Si$), 3-(N,N-dimethylaminopropyl)aminopropylmethyldimethoxysilane ($C_{11}H_{28}N_2O_2Si$), and 3-azidopropyltriethoxysilane ($C_9H_{21}N_3O_3Si$). These chemicals are listed in Tables 1A-1C in respective FIGS. 2A-2C.

Although immobilization and, particularly, bonding may be preferred strategies to prevent pathogen exposure from fabrics, hydrophobic chemical coatings that prevent bonding may be employed. These hydrophobic chemical coating materials may change the surface tension and other properties of the fabrics from hydrophilic to hydrophobic. Such coatings may repel aerosolized water droplets that may be associated with airborne pathogen transfer. The water-associated pathogens may be deterred from entering the input side of a filter, mask, or other fabric material, and/or the water-associated pathogens may be diverted from the fabrics in a manner suitable for collection, neutralization, or destruction. Some examples of hydrophobic chemicals include, but are not limited to, perfluorosilanes, nonafluorohexyltriethoxysilane ($C_{12}H_{19}F_9O_3Si$), (Tridecafluoro-1, 1, 2, 2-TetrahydroOctyl) Triethoxysilane ($C_{14}H_{19}F_{13}O_3Si$), (Heptadecafluoro-1, 1, 2, 2-Tetrahydrodecyl) Triethoxysilane ($C_{16}H_{19}F_{17}O_3Si$), and (Tridecafluoro-1, 1, 2, 2-TetrahydroOctyl) Triechlorosilane ($C_8H_4Cl_3F_{13}Si$).

The pathogen-bonding chemicals may be applied to fabrics in a variety of ways. For example, the fabrics may be dipped or immersed in a fluid of the pathogen-bonding chemical or a dilution of it. In other embodiments, the pathogen-bonding chemical or a dilution of it in a carrier fluid may be sprayed onto the fabric. These techniques may be potentially useful for fabrics such as garments and any "nonbreathable" PPE fabrics wherein there is no need for the coating to penetrate interior layers of the fabrics and coat these interior layers from all angles. A spray of liquid or aerosolized pathogen-bonding chemical may be useful in a manufacturing or commercial setting to coat nonfabric surfaces as well as fabric surfaces that are likely to come in contact with human skin. Such surfaces may include one or more of, but are not limited to, elevator buttons, mobile phones, and remote controllers. Some examples of chemicals that may be suitable for application as spray coatings to bind pathogens are shown Tables 2A-2C that show of respective FIGS. 8A-8C.

The pathogen-bonding chemicals may alternatively be applied to fabrics, particularly (but not exclusively) fabrics for air filters (including facemasks), via a vapor deposition system such as physical vapor (PVD) or chemical vapor deposition (CVD). In some embodiments, reaction chambers for one or more of low-pressure CVD, aerosol-assisted CVD, direct liquid-injection CVD, hot-wall CVD, cold-wall CVD, or plasma-enhanced CVD (PECVD) may be employed. In particular, a plasma treatment or pretreatment (e.g. a corona discharge-like treatment) renders most fabric surfaces amenable to surface modification. However, other methods of treating the fabric with the pathogen-binding chemical may be employed. One will appreciate that treating the fabrics with the pathogen-bonding chemicals in the gas phase may be advantageous to cover every surface, including the internal surfaces at every angle, down to the molecular level. A CVD may also utilize less solvents, if any, and greatly reduce the waste stream.

More generally, the pathogen-bonding chemical may be applied to a fabric at an ambient temperature and/or pressure or at a controlled temperature and/or pressure. In some embodiments, the fabric treatment may be applied at an elevated temperature. The pathogen-binding chemical may be applied to the fabric at a temperature greater than or equal to 25° C., greater than or equal to 40° C., greater than or equal to 50° C., or greater than or equal to 60° C. Alternatively or additionally, the pathogen-binding chemical may be applied to the fabric at a temperature less than or equal to 150° C., less than or equal to 125° C., less than or equal to 100° C., less than or equal to 90° C., less than or equal to 75° C., less than or equal to 60° C., or less than or equal to 50° C. In some embodiments, the pathogen-binding chemical may be applied to the fabric at a temperature greater than or equal to 25° C. and less than or equal to 100° C. or at a temperature within any range in between, especially within any range having the previously specified endpoints. One will appreciate, however, that the treatment temperature may alternatively be less than 25° C. or alternatively be greater than 150° C. In this regard, in some embodiments, the fabrics can be treated at up to the highest temperature that the fabrics and pathogen-binding chemicals can both withstand without jeopardizing their intact properties. Generally, higher temperatures may increase reaction rates, thereby reducing treatment time.

The pathogen-binding chemical may be applied to the fabric at a pressure that is less than or equal to 6666 pascals (Pa), less than or equal to 3333 Pa, less than or equal to 1000 Pa, less than or equal to 500 Pa, or less than or equal to 133 Pa. Alternatively or additionally, the pathogen-binding chemical may be applied to the fabric at a pressure greater than or equal to 1 Pa, greater than or equal to 10 Pa, or greater than 100 Pa. In some embodiments, the pathogen-binding chemical may be applied to the fabric at a pressure that is greater than or equal to 10 Pa and less than or 1333 Pa or at a pressure within any range in between, especially within any range having the previously specified endpoints. In some embodiments, the treatment may be applied to the fabric at a pressure that is greater than or equal to 1 Pa and less than or 100 Pa. One will appreciate, however, that the treatment pressure may alternatively be less than 100 Pa or alternatively be greater than 6666 Pa.

In some embodiments, the pathogen-binding chemical may be applied to the fabric at a temperature greater than or equal to 25° C. and less than or equal to 100° C. and at pressure that is greater than or equal to 10 Pa and less than or 1333 Pa. One will appreciate, however, that any combination of the above temperature and pressure ranges may be employed.

The pathogen-binding chemical treatment may be conducted in less than or equal to 2 hours, less than or equal to 1 hour, less than or equal to 45 minutes, less than or equal to 30 minutes, or less than or equal to 15 minutes. Alternatively or additionally, the pathogen-binding chemical may be conducted in greater than or equal to 5 minutes, greater than or equal to 10 minutes, or greater than or equal to 15 minutes. In some embodiments, the pathogen-binding chemical treatment may be conducted in greater than or equal to 10 minutes and less than or equal to 30 minutes, or at a time period within any range in between, especially within any range having the previously specified endpoints. One will appreciate, however, that the pathogen-binding chemical treatment may alternatively be conducted for less than 5 minutes or may alternatively be conducted for greater than 2 hours. One will appreciate that much of the treatment time involves waiting for the reaction chamber to reach the desired vacuum pressure and that the overall treatment time may be reduced as the size and efficiency of the vacuum pump is increased.

The fabric may be treated until it is saturated the pathogen-binding chemical. In other words, in general the fabric does not exhibit significant increase in total binding of the pathogen-binding chemical regardless of exposure to increased concentrations of the pathogen-binding chemical or increased treatment time. Accordingly, concentrations of pathogen-binding chemical used for treatment of fabrics may be (but need not be) quite small. Moreover, the amount of pathogen-binding chemical used for treatment of fabrics does not require precise control or monitoring. The actual concentration of pathogen-binding chemical in the reaction chamber may be dependent on the temperature and pressure within the reaction chamber.

The pathogen-binding chemical may form a coating that has a depth of less than or equal to 10 nanometers (nm), less than or equal to 5 nm, less than or equal to 2 nm, less than or equal to 1 nm, or less than or equal to 0.5 nm. Many pathogen-binding chemicals may form a coating that has a depth in a range between 0.5 nm and 2 nm; however, ranges between any of these endpoints may be possible. One will also appreciate that some pathogen-binding chemicals may form a coating with a depth greater than 10 nm.

In some embodiments, the coating may employ individual pathogen-binding chemicals that bind to the fabric and not to each other, or the coating may employ individual pathogen-binding chemicals that bind to the fabric as well as to each other. Thus, some crosslinking of the pathogen-binding chemicals may occur. Generally, more than 50% of the pathogen-binding chemicals that are bound to the fabric are crosslinked to fewer than or equal to 5 of the same pathogen-binding chemicals, more than 75% of the pathogen-binding chemicals that are bound to the fabric are crosslinked to fewer than or equal to 5 of the same pathogen-binding chemicals, or more than 90% of the pathogen-binding chemicals that are bound to the fabric are crosslinked to fewer than or equal to 5 of the same pathogen-binding chemicals. In some embodiments, more than 50% of the pathogen-binding chemicals that are bound to the fabric are crosslinked to fewer than or equal to 3 of the same pathogen-binding chemicals, more than 75% of the pathogen-binding chemicals that are bound to the fabric are crosslinked to fewer than or equal to 3 of the same pathogen-binding chemicals, or more than 90% of the pathogen-binding chemicals that are bound to the fabric are crosslinked to fewer than or equal to 3 of the same pathogen-binding chemicals.

For convenience, the coating may be considered to be a layer that may be noncontiguous with an average depth within the above ranges. Moreover, the layer may have a substantially uniform depth, or the layer may deviate substantially from the average depth.

The pathogen-binding chemicals bond to the fabric in a manner that does not impede airflow. In particular, untreated fabrics and fully saturated fabrics showed no change in airflow detectable by an airflow meter. Airflow tests employed a fan in a small box having a 5.08 cm×5.08 cm (2 inch×2 inch) opening for insertion of a manometer tube for a Retrotec DM32 manometer. The airflow (cubic feet per minute) was measured of the fan without a clinical mask, with an uncoated clinical mask, and with a clinical mask coated with pathogen-binding chemical. The difference in airflow through the untreated mask and the treated mask was undetectable.

The fabrics may be treated with the pathogen-binding chemicals in discrete batches or in a flow-through process. The fabric may also be treated with multiple different pathogen-binding chemicals. For example, two or more pathogen-binding chemicals may be applied to a fabric, or three or more pathogen-binding chemicals may be applied to a fabric. These treatments may be simultaneous, partly overlapping, or discretely sequential.

In some embodiments wherein two or more pathogen-binding chemicals are applied to a fabric, a first pathogen-binding chemical may be selected for higher capability for binding virus and second pathogen-binding chemical may be selected for higher capability for binding bacteria, fungus, and/or IgG. In other embodiments wherein two or more pathogen-binding chemicals are applied to a fabric, a first pathogen-binding chemical may be selected for higher capability for binding to a first type of virus coat protein and second pathogen-binding chemical may be selected for higher capability for a second different type of virus protein. In yet other embodiments wherein two or more pathogen-binding chemicals are applied to a fabric, a first pathogen-binding chemical may be selected for higher capability for binding to a first specific virus (or type of virus) and second pathogen-binding chemical may be selected for higher capability for a second different specific virus (or type of virus).

The pathogen-binding chemicals may be heated or vaporized in a vaporization chamber that is discrete from the fabric treatment chamber. Vaporization may occur in the absence or presence of a carrier fluid, which may be a liquid or a gas. Carrier fluids may include one of more of nitrogen or an inert gas, such as argon, helium, xenon, krypton, and neon.

The fabrics may be pretreated to enhance the surface attachment of the pathogen-binding chemicals. Examples of fabric pretreatments include, but are not limited to, fabric exposure to oxygen, water, or alcohol. Exposure may include a soaking, rinsing, or treatment in a low-pressure discharge chamber. Some fabric pretreatments may include sequential treatments by multiple different substances. In some embodiments, sequential treatment with oxygen and then water or alcohol may be employed. In some embodiments, sequential treatment with oxygen followed by water and then followed by alcohol may be employed. Purges are not necessary between the pretreatments, and purges are not necessary between the pretreatment and the application of the pathogen-binding chemical. However, evacuation to vacuum base pressure between the pretreatments, and between the pretreatment and the application of the pathogen-binding chemical, may be employed.

The pretreatment(s) may be applied to the fabric at a pressure that is less than or equal to 6666 pascals (Pa), less than or equal to 3333 Pa, less than or equal to 1000 Pa, less than or equal to 500 Pa, or less than or equal to 133 Pa. Alternatively or additionally, the pretreatment(s) may be applied to the fabric at a pressure greater than or equal to 1

Pa, greater than or equal to 10 Pa, or greater than 100 Pa. In some embodiments, the pretreatment(s) may be applied to the fabric at a pressure that is greater than or equal to 10 Pa and less than or 1333 Pa or at a pressure within any range in between, especially within any range having the previously specified endpoints. In some embodiments, the pretreatment(s) may be applied to the fabric at a pressure that is greater than or equal to 1 Pa and less than or 100 Pa. One will appreciate, however, that the pretreatment pressure may alternatively be less than 100 Pa or alternatively be greater than 6666 Pa. One will also appreciate that the pretreatments may be applied at about the same pressure or at different pressures.

In some embodiments, a vapor adhesion layer may be introduced after the pretreatment(s) and before the pathogen-bonding chemical vapor is applied. A vapor adhesion layer may include one or more of a metal oxide, such as aluminum oxide, silicon oxide, or titanium oxide. Employing a vapor adhesion layer may provide better surface adhesion to some fabrics. However, the potential small adhesion gain by employing a vapor adhesion layer may not justify the added cost and time, especially in view of the utility of the above-described pretreatment(s).

Some suitable multifunctional silanes were identified and their utility was verified using the material-coating procedures and protein-binding assays as described below. In some example experiments, a coating method employed a sub-atmospheric gas-phase flow-through pressure reactor suitable for large batch processing. In this regard, commercially available equipment (Model RPX-540) from Integrated Surface Technologies, located at 3475-Edson Way, Menlo Park, CA, 94025, USA, was employed for chemical vapor deposition to apply nano-coating to selected materials, including microtiter plates and fabrics.

Various ones of the chemicals listed in Tables 1A-1C shown in respective FIGS. 2A-2C were independently vaporized into a temperature-controlled reaction vessel typically between 40 and 75° C. The partial pressure of the chemical vapors was metered to ensure no liquid condensation onto the articles of fabric and other materials.

A plasma-enhanced chemical vapor deposition (PECVD) technique was used to deposit nano-thick pathogen-binding chemicals, such as bioactive silane molecules onto various material substrates including fabrics of personal protective equipment such as facemasks. The substrates were first pretreated with a plasma cleaning step (a low-pressure glow discharge with oxygen, water, and/or alcohol, sequentially) to remove contaminants and/or enhance the surface attachment of the chemicals. In some particular examples, a first pretreatment employed a plasma discharge of oxygen (6.66-26.66 Pa (~50-200 mtorr)) for 2 to 15 minutes at 50-400 Watts (40 kHz or 13.56 MHz) and a second pretreatment employed a plasma discharge of water (6.66-26.66 Pa (~50-200 mtorr)) for 2 to 15 minutes at 20-200 Watt (40 kHz or 13.56 MHz).

Each bioactive silane molecule was evaporated with a thermal process and injected into the PECVD chamber using carrier gas (02 and/or Argon). The reduced pressure reactor allowed for the surface modification reactions to occur between 0.1 to 10 Torr as controlled by a vacuum pump. The reactions typically took more than 5 minutes and less than 30 minutes to complete. At the end of the reaction time, the reactor vessel was purged with $N_2$ to remove any excess or unreacted vapors (which can be saved and used in subsequent runs).

Assays were used to determine the ability of the coated material to capture virus. In one experiment, non-protein binding 96-well microtiter plates (Corning, catalogue #3641) were nano-coated with various chemicals. Uncoated microtiter plates (Corning, catalogue #3641) and high-protein-binding ELISA plates (Corning, catalogue #9017) were used for comparison.

Human IgG (R&D Systems, catalogue #1-001-A) was initially used as a chemistry screening tool to narrow the scope of chemistries to be tested for capture of the novel coronavirus spike protein and then later used in tests for comparison and as a model for binding bacterial pathogens. Purified SARS-CoV-2 spike protein was applied directly (in duplicate experiments) to the controls and the ones treated with the chemicals listed in Tables 1A-1C. This procedure was performed at a fixed concentration or in serial dilutions of the viral protein for various time points to determine kinetics of protein capture. A solution with no protein served as an additional control. The tested articles were washed before analysis. In particular, the tested articles were washed with phosphate buffered saline (PBS) three times for 5 minutes each wash; however, one will appreciate that different wash solutions, different number of washes, and/or different time periods may be employed.

Quantitation of viral protein or IgG capture was determined by using a standard enzyme-linked immunosorbent assay (ELISA) format with an anti-spike protein-Fc reagent and a secondary antibody to crystallizable fragment (Fc) conjugated to horseradish peroxidase (HRP) followed by development with a tetramethylbenzine (TMB) reagent that was detected with spectrophotometry (absorption at 450 nm).

FIG. 3 is bar graph showing the relative binding of SARS-CoV-2 spike protein and IgG applied independently in a fixed concentration to control plates and microtiter plates treated with a different one of four of the bifunctional silane chemicals listed in Tables 1A-1C. With reference to FIG. 3, the developed test plates subjected to nonprotein solution showed only background binding and no significant differences between the different samples. The uncoated microtiter plates did not capture either the SARS-CoV-2 spike protein or IgG. The control high-protein-binding plate bonded to the two proteins relatively equally but bonded them less efficiently than the test plates coated with the example four bifunctional silane molecules.

Figure 4A:
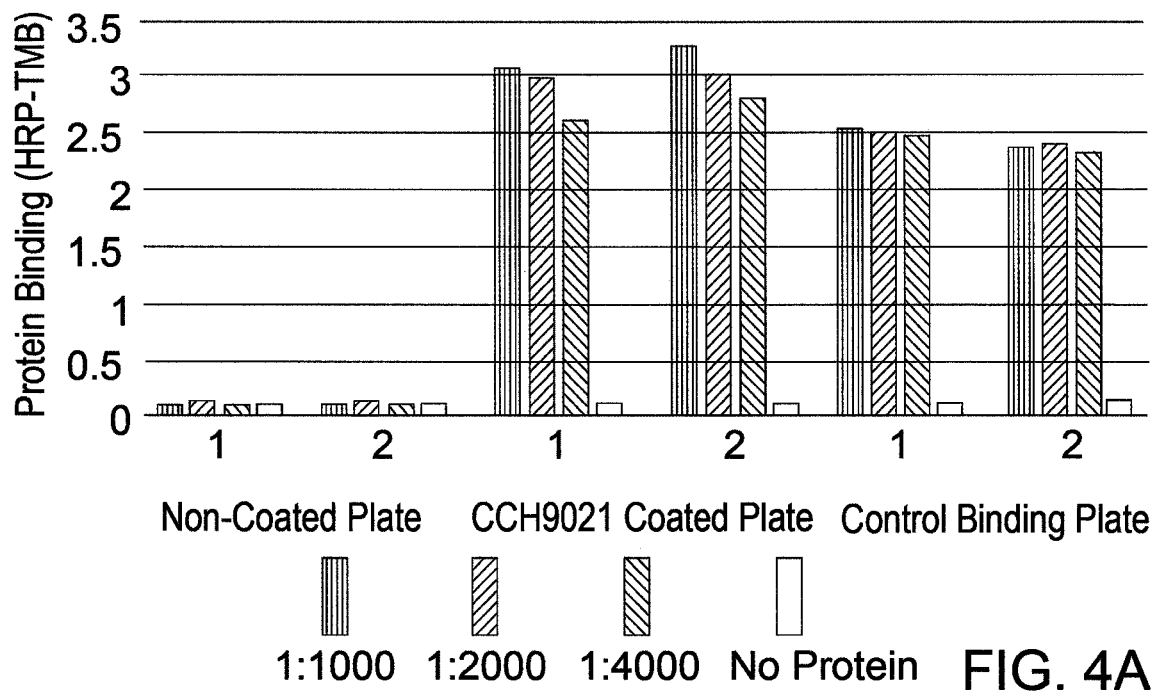
FIGS. 4A and 4B are bar graphs showing the relative binding of IgG applied at different concentrations to microtiter plates treated with N-(2-aminoethyl)-3-aminopropyltriethoxysilane ($C_{11}H_{28}N_2O_3Si$).
Figure 4B:
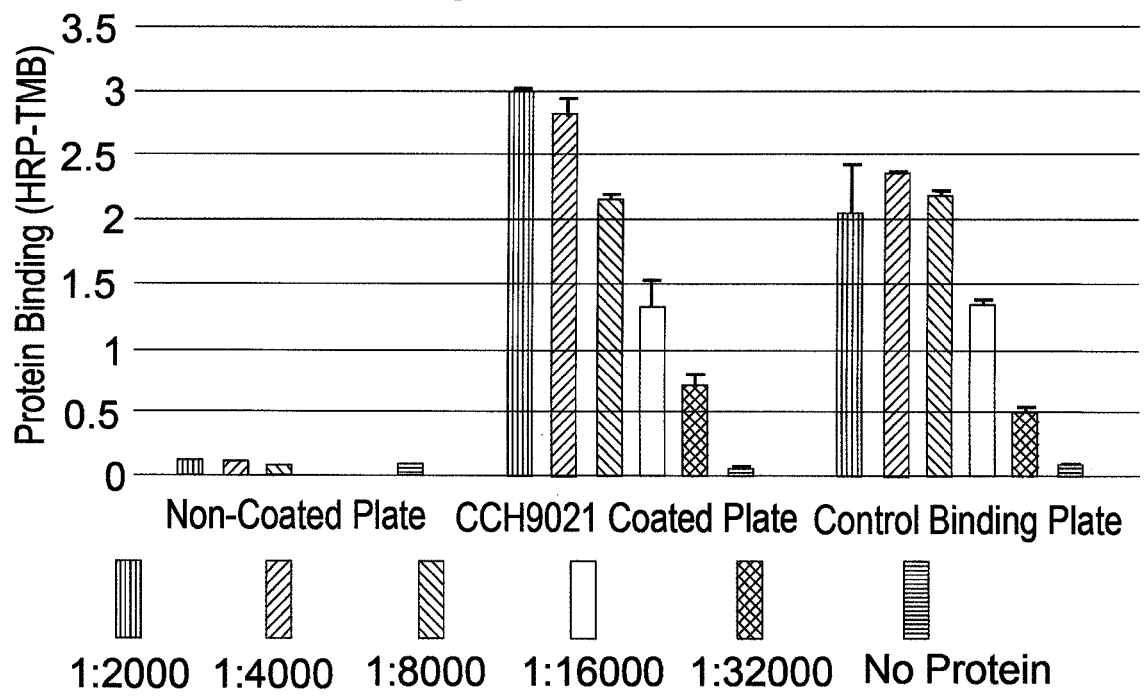

FIGS. 4A and 4B are bar graphs showing the relative binding of IgG applied at different concentrations to microtiter plates treated with N-(2-aminoethyl)-3-aminopropyltriethoxysilane ($C_{11}H_{28}N_2O_3Si$), one of the bifunctional silane chemicals listed in Tables 1A-1C. In particular, FIG. 4A shows duplicative tests of exposure to IgG at three concentrations, and FIG. 4B shows a replicative experiment that includes greater dilutions. 50 microliters (mL) of each solution was applied to the wells. The initial concentration of IgG started at 1 μg/ml. At all concentrations, the uncoated plate showed only background bonding and no significant differences between the different concentration exposures and no significant differences with the nonprotein exposures. Moreover, at all concentration levels that included IgG, the plates coated with N-(2-aminoethyl)-3-aminopropyltriethoxysilane ($C_{11}H_{28}N_2O_3Si$) significantly outperformed the high-protein-binding ELISA plates.

FIG. 5 is a bar graph showing the relative binding of SARS-CoV-2 spike glycoprotein applied at different concentrations to microtiter plates treated with a different one of three of the bifunctional silane chemicals listed in Tables 1A-1C. The high-protein-binding ELISA plate and the chemically coated plates showed little significant difference to the nonprotein solution. At the 100 ng/ml concentration of SARS-CoV-2 spike glycoprotein applied to the test plates, the chemically coated plates all outperformed the high-protein-binding ELISA plate. At the 33 ng/ml concentration of SARS-CoV-2 spike glycoprotein applied to the test plates, the CCH4502 and CCH1053 chemicals outperformed the high-protein-binding ELISA plate, but the CCH9021 chemical slightly underperformed the high-protein-binding ELISA plate. At the 11 ng/ml and 3.3 ng/ml concentrations of SARS-CoV-2 spike glycoprotein applied to the test plates, the high-protein-binding ELISA plate outperformed all of the chemically coated plates. Additionally, glycoprotein capture was resistant to low pH washes (data not shown), suggesting some compounds have extremely high affinity, and potentially irreversible, bonding.

FIG. 6 is a bar graph showing the relative binding of SARS-CoV-2 spike glycoprotein applied at different concentrations to microtiter plates treated with a different one of four other of the bifunctional silane chemicals listed in Tables 1A-1C. The chemical coatings employing chemicals CCH17654 and CCH51082 significantly outperformed the control high-protein-binding ELISA plate. The chemical coating employing the chemical CCH288550 showed almost the same performance as the control high-protein-binding ELISA plate. However, the control high-protein-binding ELISA plate significantly outperformed the chemical coating employing the chemical CCH699020.

Overall, with reference again to FIGS. 2A-2C, both CCH4502 and CCH1053 were marginally but consistently more capable of binding the coronavirus spike protein than CCH9021. CCH8845 appeared to bind about equally well as CCH9021, CCH4502, and CCH1053. CCH51082 and CCH17654 bound the coronavirus spike protein significantly better than CCH9021.

Without being bound to any particular theory, it may be possible to interpret some of the results. CCH9021, CCH1053, and CCH17654 all contain amino groups that may bind non-covalently to negative charges on the protein or to sugars. CCH4502 contains an epoxy group that may facilitate covalent binding to amine, serine, tyrosine, and/or cysteine on protein or to phospholipids. CCH8845 contains a C=C double bond that may react covalently or noncovalently with amine groups on the pathogen protein; moreover, the carboxyl group may react covalently or noncovalently with amines on the pathogen protein. Difference in potency between CCH9021 and CCH699020 could be explained if the carbon chain length between the primary and secondary amines impacts binding to the protein. CCH17654 is more potent than CCH9021, possibly explained by a larger chemistry attached to the CCH17654, making the reactive group more accessible for binding.

Figure 7:
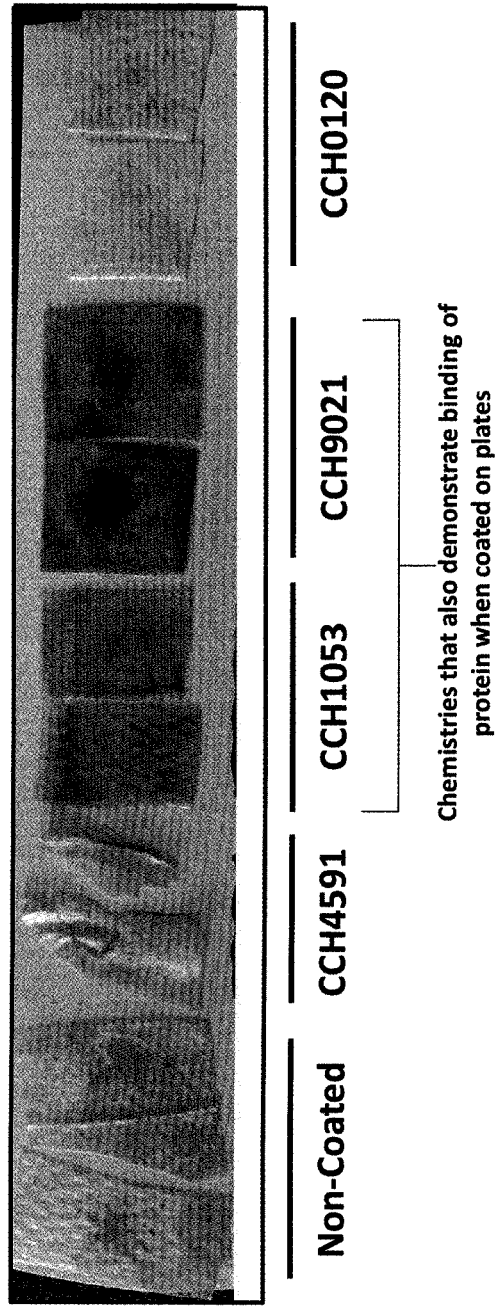
FIG. 7 depicts the relative binding of a model protein to pieces of facemasks coated with a different one of three bifunctional silane chemicals as well as to uncoated and hydrophobic controls.

FIG. 7 depicts the relative binding of a model protein to pieces of facemasks coated with a different one of three bifunctional silane chemicals as well as to uncoated had hydrophobic controls. With reference to FIG. 7, pairs of pieces of standard facemasks (Machimpex, catalogue #1005-544-988) were nanocoated with one of the various chemicals. One pair, shown at the far left, was left uncoated. One pair, shown at the far right was nanocoated with a hydrophobic chemical, CCH0120, that repels protein binding. IgG was used as a model for protein capture as it behaved similar to the full-length coronavirus spike protein in plate-binding assays and is likely to have similar activity to that of bacterial coat proteins. The IgG was applied to the facemask fabric and incubated for 30 minutes prior to washing in phosphate buffered saline (PBS). Detection of the captured protein after washing was performed by applying 200 µl Gel-Code protein staining dye (Thermo Fisher Scientific, catalogue #24590) directly to the materials and incubating for one hour. Color change indicating protein capture was documented by photography. As seen in FIG. 7, both CCH1053 and CCH9021 efficiently captured the protein onto facemask relative to the uncoated facemask. Visually, the NCT9021 compound appears to have captured more efficiently.

These data lend support to the notion that multiple materials, including fabrics such as filters and other PPE, coated with bio-reactive chemicals enable the treated fabrics to efficiently and rapidly capture pathogens from the air or contaminated surfaces. Moreover, airborne pathogens are prevented from passing through these treated fabrics because the pathogens become entrapped in the fabric and ultimately perish. A primary benefit of the treated fabrics is that they can protect users from exposure to contagious airborne pathogens. A secondary benefit of these treated fabrics is that they facilitate safe handling during replacement and disposal after the fabrics are contaminated because the nano-coated PPE's and air filters have captured the pathogens, preventing them from re-aerosolizing upon handling. Finally, treatment of these fabrics with the pathogen-binding chemicals disclosed herein adds only a fractional cost to these components and is well-justified given the potential impact on viral and bacterial spread.

CONCLUSION

The terms and descriptions used above are set forth by way of illustration and example only and are not meant as limitations. Those skilled in the art will recognize that many variations, enhancements and modifications of the concepts described herein are possible without departing from the underlying principles of the invention. For example, skilled persons will appreciate that the subject matter of any sentence or paragraph can be combined with subject matter of some or all of the other sentences or paragraphs, except where such combinations are mutually exclusive.

The scope of the invention should therefore be determined only by the following claims, claims presented in a continuation patent application, and equivalents to the foregoing claims.

The invention claimed is:

1. A pathogen-capturing material for binding airborne pathogens, comprising:
a fabric treated with a pathogen-binding chemical, wherein the fabric is configured in a form of a filter medium configured to allow air to pass therethrough, wherein the pathogen-binding chemical comprises a multifunctional molecule, including at least a first functional group and a second functional group, wherein the first functional group is bonded to the fabric and the second functional group is configured to bond to a protein-encapsulated airborne pathogen, and wherein the multifunctional molecule comprises a multifunctional alkoxysilane.

2. The pathogen-capturing material of claim 1, wherein the filter medium is configured in the form of a mask or configured for employment in an air circulation system.

3. The pathogen-capturing material of claim 1, wherein the pathogen-binding chemical comprises a trialkoxysilane, a triethoxysilane, a trimethoxysilane, or a dimethoxysiliane.

4. The pathogen-capturing material of claim 3, wherein the pathogen-binding chemical comprises an aminosilane.

5. The pathogen-capturing material of claim 1, wherein the pathogen-binding chemical comprises a multifunctional silane that includes an aliphatic linker of 2 to 18 atoms between a silicon atom and one or more terminal functional groups, and wherein atoms in the linking chain are predominately carbon, and wherein the aliphatic linker is flexible.

6. The pathogen-capturing material of claim 5, wherein the linking chain contains one or more of oxygen, nitrogen, sulfur, a bis amine, or a phenyl group and/or the terminal groups includes a simple amine.

7. The pathogen-capturing material of claim 1, wherein the pathogen-binding chemical comprises 3-aminopropyltriethoxysilane ($C_9H_{23}NO_3Si$), (3-glycidoxypropyl)trimethoxysilane ($C_9H_{20}O_5Si$), N-(2-aminoethyl)-3-aminopropyltriethoxysilane ($C_{11}H_{28}N_2O_3Si$), 3-aminopropyltrimethoxysilane ($C_6H_{17}NO_3Si$), triethoxysilylpropylmaleamic acid ($C_{13}H_{25}NO_6Si$), (aminoethylaminomethyl)phenethyltrimethoxysilane ($C_{14}H_{26}N_2O_3Si$), 3-(N,N-dimethylaminopropyl)aminopropylmethyldimethoxysilane ($C_{11}H_{28}N_2O_2Si$), or 3-azidopropyltriethoxysilane ($C_9H_{21}N_3O_3Si$).

8. The pathogen-capturing material of claim 1, wherein the pathogen-binding chemical is covalently and/or exothermically bonded to the fabric and the pathogen-binding chemical is configured to covalently and/or exothermically bond to a virus and IgG.

9. The pathogen-capturing material of claim 1, wherein the pathogen-binding chemical is configured to bond to a spike protein of a virus, a membrane protein of a virus, an envelope protein of a virus, or a phospholipid bilayer of a virus.

10. The pathogen-capturing material of claim 1, wherein the treated fabric has a coating of the pathogen-binding chemical with a depth of less than or equal to 2 nm.

11. The pathogen-capturing material of claim 1, wherein the treated fabric has a coating of the pathogen-binding chemical that is noncontiguous.

12. The pathogen-capturing material of claim 1, wherein more than or equal to 90% the pathogen-binding chemicals bound to the fabric are crosslinked to fewer than or equal to 5 of the same pathogen-binding chemicals.

13. The pathogen-capturing material of claim 1, wherein more than or equal to 75% the pathogen-binding chemicals bound to the fabric are crosslinked to fewer than or equal to 3 of the same pathogen-binding chemicals.

14. The pathogen-capturing material of claim 1, wherein the fabric before and after treatment with the pathogen-binding chemical exhibits no difference in airflow as detected by a Retrotec DM32 manometer.

15. The pathogen-capturing material of claim 1, wherein treatment of the fabric with the pathogen-binding chemical results in non-toxic reaction biproducts below their toxicity threshold limit values (TLVs) to humans.

16. The pathogen-capturing material of claim 1, wherein the treated fabric has a coating of the pathogen-binding chemical with a depth of less than or equal to 5 nm, and wherein more than or equal to 50% the pathogen-binding chemicals bound to the fabric are crosslinked to fewer than or equal to 5 of the same pathogen-binding chemicals.

17. The pathogen-capturing material of claim 1, wherein the fabric has first and second sides configured to permit air to enter through the first side and exit from the second side, such that air having a measurable amount of protein-encapsulated airborne pathogens that are contagious to humans flowing through the first side contains no measurable amount of protein-encapsulated airborne pathogens that are contagious to humans upon exiting from the second side.

18. The pathogen-capturing material of claim 1, wherein the fabric is optionally pretreated with oxygen, and wherein the pathogen-binding chemical is preheated before being applied to the fabric in a plasma process or a corona discharge process in a chemical vapor deposition (CVD) chamber, a plasma-enhanced chemical vapor deposition (PECVD) chamber, or a sub-atmospheric gas-phase flow-through reactor.

19. The pathogen-capturing material of claim 18, wherein the pathogen-binding chemical is applied to the fabric at a temperature greater than or equal to 25° C., at a temperature less than or equal to 150° C., or at a temperature greater than or equal to 25° C. and less than or equal to 150° C., and wherein the pathogen-binding chemical is applied to the fabric at a pressure less than or equal to 500 Pa.

20. The pathogen-capturing material of claim 1, wherein the pathogen-binding chemical comprises an aminosilane in the form of a trialkoxysilane, a triethoxysilane, a trimethoxysilane, or a dimethoxysiliane, wherein the treated fabric has a coating of the pathogen-binding chemical with a depth of less than or equal to 5 nm, wherein more than or equal to 50% the pathogen-binding chemicals bound to the fabric are crosslinked to fewer than or equal to 5 of the same pathogen-binding chemicals, and wherein the fabric before and after treatment with the pathogen-binding chemical exhibits no difference in airflow as detected by a Retrotec DM32 manometer.

* * * * *